(12) United States Patent
Wharton et al.

(10) Patent No.: US 7,686,016 B2
(45) Date of Patent: Mar. 30, 2010

(54) MEDICATION HOLDER

(75) Inventors: David Peter Wharton, Bribie Island (AU); Ben Huber, Clayfield (AU)

(73) Assignee: Medi-Stream Pty Ltd ACN 111 815 715, Bowen Hills, QLD (AU)

( * ) Notice: Subject to any disclaimer, the term of this patent is extended or adjusted under 35 U.S.C. 154(b) by 987 days.

(21) Appl. No.: 10/573,344

(22) PCT Filed: Sep. 24, 2004

(86) PCT No.: PCT/AU2004/001316

§ 371 (c)(1),
(2), (4) Date: Mar. 24, 2006

(87) PCT Pub. No.: WO2005/028006

PCT Pub. Date: Mar. 31, 2005

(65) Prior Publication Data

US 2007/0119450 A1 May 31, 2007

(30) Foreign Application Priority Data

Sep. 24, 2003 (AU) ............... 2003905192
Mar. 26, 2004 (AU) ............... 2004901625

(51) Int. Cl.
*A61M 11/00* (2006.01)
(52) U.S. Cl. ............... 128/202.13; 128/200.14
(58) Field of Classification Search ............ 128/202.13, 128/200.14, 200.23, 204.23
See application file for complete search history.

(56) References Cited

U.S. PATENT DOCUMENTS 4,130,116 A 12/1978 Cavazza
5,497,764 A 3/1996 Ritson et al.
5,501,236 A 3/1996 Hill et al.

(Continued)

FOREIGN PATENT DOCUMENTS

BE 905189 A 1/1987

(Continued)

OTHER PUBLICATIONS

Nicorette Inhaler Instruction Booklet.

*Primary Examiner*—Steven O Douglas
(74) *Attorney, Agent, or Firm*—Greenberg Traurig LLP

(57) ABSTRACT

A medication holder is disclosed comprising a housing (10) having an outer wall (12) and an inner wall (11) preferably in sleeved relationship to each other. The outer wall may be moved between a closed position in which the housing (10) is sealed for ingress of moisture or other contaminants and an open position providing access to the medication container discharge outlet. The second wall may (12) be slid longitudinally or rotated circumferentially to access the cavity and may, in the process, open an air pathway through the cavity. The medication container is preferably a pressurized canister (22). Alternatively, it may comprise a frangible vial (603) with a volatile liquid. In the latter case, an evaporation grid (563) may also be supplied to enhance absorption of the liquid which is preferably methoxyfluorane. Opening means (561) may be provided to open the frangible vial and discharge the contents onto the evaporation means (563) which is in fluid contact with the air pathway (806). A medication chute (26) may be rotatable between stowed and deployed positions. The chute (26) may include an auxiliary air inlet (556). The medication holder may also include one-way valves (605) to channel inspiratory air through the chamber and direct expiratory air elsewhere. The expiratory air may pass through unidirectional valve (810) and also through an absorbent filter (805) to minimize environmental contamination.

25 Claims, 30 Drawing Sheets

U.S. PATENT DOCUMENTS

| | | |
|---|---|---|
| 5,522,378 A | 6/1996 | Ritson et al. |
| 5,622,162 A | 4/1997 | Johansson et al. |
| 5,755,218 A | 5/1998 | Johansson et al. |

FOREIGN PATENT DOCUMENTS

| | | |
|---|---|---|
| CA | 2379137 A1 | 2/2001 |
| DE | 4028387 A | 3/1992 |
| EP | 1386630 A1 | 2/2004 |
| WO | WO 95/28192 A1 | 10/1995 |
| WO | WO 00/18455 A1 | 4/2000 |
| WO | WO 01/00263 A2 | 1/2001 |
| WO | WO 02/04043 A2 | 1/2002 |
| WO | WO 03/095010 A2 | 11/2003 |

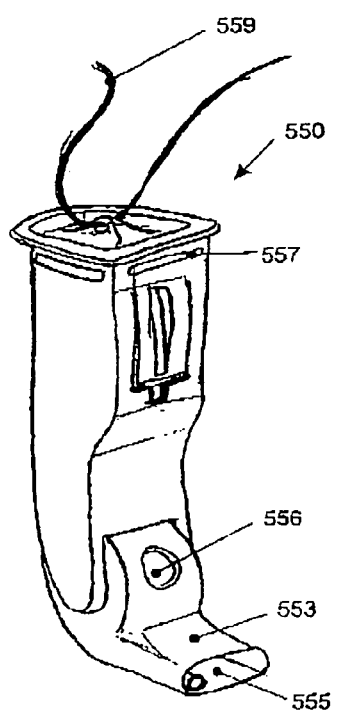
FIGURE 33A.
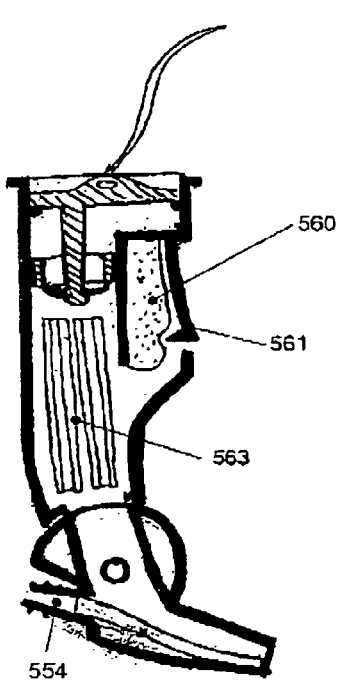
FIGURE 33B.
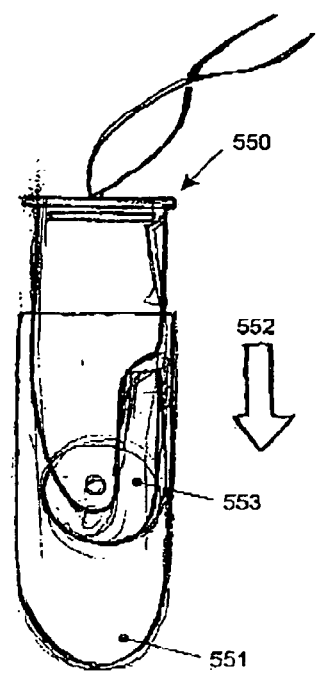
FIGURE 33C.
FIGURE 33.

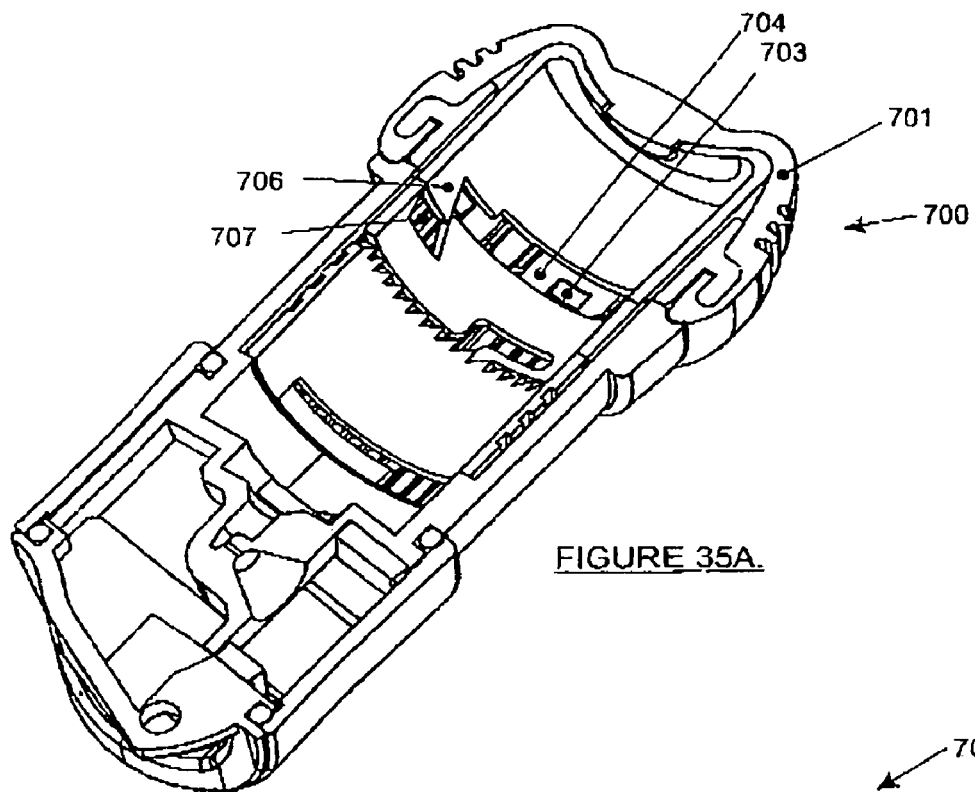
FIGURE 35A.
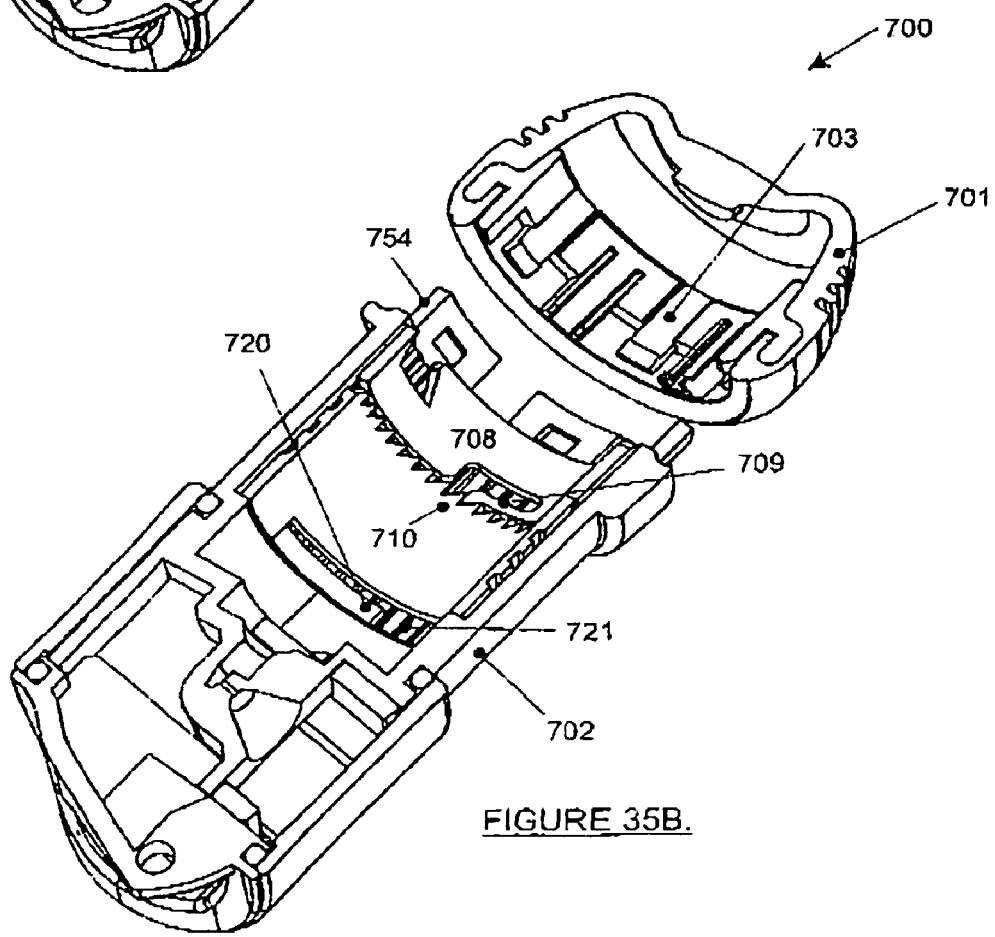
FIGURE 35B.
FIGURE 35.

MEDICATION HOLDER

This application is a national stage filing under 35 U.S.C. 371 of International Application PCT/AU2004/001316 filed on Sep. 24, 2004 which claims priority from Australian Patent Application No: 2003905192, filed on Sep. 24, 2003 and Australian Patent Application No: 2004901625 filed Mar. 26, 2004. The entire teachings of these referenced applications are incorporated herein by reference. International Application PCT/AU2004/001316 was published under PCT Article 21(2) in English.

FIELD OF THE INVENTION

THIS INVENTION relates to a device for securely storing or receiving a container holding medication for use by a person. In particular, the invention relates to a device for holding and dispensing medication provided for inhalation or ingestion. The device is particularly suitable for use by a person when mobile and/or in an adverse environment and may be well suited for use during sporting activities, but is not so limited. Operation of the device facilitates access to the medication for administration. The invention extends to a medication holder including a reservoir or container of medication.

BACKGROUND OF THE INVENTION

The evolution of devices for self-medication has been of great advantage to sufferers of various diseases and pathologies.

One prime example is that of asthma in earlier times, sufferers of asthma were typically sentenced to a lifetime of disability, often based on arranging their life around low levels of physical activity or restricted ranges of travel, so that they could be close to support mechanisms provided in their own environment. Severe bouts of asthma often required the attention of professionals, such as doctors, and the use of drugs administered by those professionals. These drugs, which included aminophylline and adrenaline, had reasonable levels of efficiency but also brought with them some significant risks in use. Further, the use of these drugs was a late stage step in the process and did not provide any ongoing advantage to a patient in the way of control and stabilization of the disease condition.

The development of corticosteroids was of great assistance in some diseases and, in particular, asthma. However, the side effects of prolonged oral or parenteral administration of corticosteroids in people are notorious and necessitate restrictions on the adoption of this approach in other than the most severe cases.

A dramatic improvement in the quality of life of sufferers of asthma arose with the development of pressurized medicated containers designed, in part, for the self-administration of salbutamol, a bronchodialator, which is very effective in counteracting the bronchospasm of an asthma attack. Salbutamol is usually provided in a pressurized container with a depression-activated valve at its top. The valve is configured to nest in a seat provided on an outer plastic collar, cap or mouthpiece. This collar allows the depression of the canister relative to a valve stem, thereby releasing a controlled dose of therapeutic agent into a discharge throat of the collar. A patient uses the device by exhaling to a required extent and then inhaling while depressing the canister to discharge a dose of the agent.

As well as providing the ability to treat an attack of respiratory embarrassment, the salbutamol inhalers have provided the ability to self-administer a regime of treatment to thereby minimize clinical signs and allay or prevent further development of the respiratory attack.

Salbutamol is an excellent example of a suitable therapeutic agent for self-delivery but is by no means alone. Many other forms of therapy have been provided for asthma (for example, Becotide, Flexitide, Asmol). Additionally, many other diseases lend themselves to self-medication through the provision of a metered dose, either into the respiratory tract or for ingestion through the gastrointestinal tract or absorption through the mucous membranes of the oropharynx or the nose. Certain analgesics may also be provided for use in emergency situations. For instance, it is known to provide methoxyfluorane to victims of trauma, either accidental or inflicted on a battlefield.

Provision of the medication may be in a form as described, being a compressed pressurized aerosol formulation often in a form known as metered-dose inhalers or MDIs. Alternatively, powder or other solid formulations or even liquids or gases may be provided and dispensed at a set dose. Liquids may be of a volatile nature. Separate individual doses of medication may be provided in a capsule or similar form and adapted for release in devices often referred to as medihalers. These devices may have rotatable vanes which are activated by a patient breathing in, thereby distributing the medication into the airstream. In some arrangements, a fine powder may be simply breathed into the lungs after separation into individual particles and entrainment in inspiratory gases.

While these developments have been of tremendous benefit to sufferers of diseases that lend themselves to effective self-medication, there has been an ongoing problem of patients either forgetting their medication canisters or mistakenly believing they are stored somewhere, such as a handbag or sports bag, only to find the medication is not available for use when required. This can have serious consequences in the event of a sudden severe onset of disease signs and symptoms. The problem of effectively and safely storing medication canisters is exaggerated in sporting activities where clothes are often designed for the specific requirements of the sport being undertaken, but with no provision of secure pockets or pouches. Even when pockets are provided, the presence of a hard object carried in such a pocket may be uncomfortable, irritating or even performance-restricting in a competitor. The problems may be pronounced in activities, such as snorkeling, scuba diving, orienteering and mountaineering where a sufferer of a condition may find themselves a considerable distance from a support base with little else other than gear required for the activity.

Use in harsh environments or inclement conditions, such as rain and snow, may lead to ingress of moisture and other contaminants, such as mud, dust, sand, vegetable matter or other materials that may damage a medication device or present a risk to the user.

U.S. Pat. No. 4,130,116 ("Cavazza") describes a pocket device into which a spray can may be inserted. Mechanical means are provided wherein the device may be kept in a closed position when not in use but can be activated to expose the nozzle portion of the spray can to permit utilization of the can. The disclosure is to two halves that slide with respect to each other along guides located along borders of the lateral walls. There is no indication that the device is sealed against moisture and, in its operation, a wide aperture is presented to the environment both at the first nozzle end and second actioning end. The application of the device is therefore somewhat limited, particularly in inclement environments, such as are often encountered during sporting activities, particularly waterborne sports and endurance type activities.

CA 2,379,137 ("Pharmaceutical Discovery Corporation") describes a dry powder inhaler having an intake section, a mixing section and a rotatable mouthpiece. The device is relatively complex, although it does include a storage section for holding an extra medicament capsule. The device is particularly directed towards controlling a rate of airflow using a tapered piston rod and spring and one or more bleed-through orifices. It may also include a feedback module to generate a tone indicating when a proper rate of airflow has been achieved. Again, there is no indication that this device is environmentally sealed. It appears to be relatively bulky and complex in operation. Further, a person in shock or respiration distress may be unable to provide the necessary inspiratory effort.

U.S. Pat. No. 5,497,764 ("Ritson") is directed to a portable battery powered handheld system for releasing a controlled dose of aerosol medication for inhalation by a patient. The device includes a durable body and a medication cassette inserted in the durable body. Although the disclosure is to an electronic and relatively complex apparatus, it does disclose formation of a cassette for insertion inside the device which is constructed so that it can be used as a conventional, manually actuated metered dose inhaler device apart from the durable body. This, however, requires removal of the device from the body for its function. When housed in the durable body, the operation of the device is relatively complex. The pharmaceutical formulations may be a liquid or powder formulation. The device is not environmentally sealed. It appears relatively complex and is predominantly electronic.

BE 905189 ("Glaxo Group Ltd") is directed to a device for administering medicaments in solid finely divided form to patients. The device is relatively complex, having a housing and a tray with a support disk provided on the tray and adapted to receive a carrier which, in turn, carries the medication. A plunger is operable to penetrate the container after it is aligned with the plungers. Air enters through the device and is inhaled.

DE 4028387 ("Bechter") discloses a cover device that dissembles to provide a breathing mask with free space over the nose and chin. It is therefore relatively large. It is designed in one embodiment as a breathing mask for use with inhalation apparatus.

The device is therefore developed as a breathing mask for use in conjunction with an inhalation apparatus.

WO 01/00263 ("Inhale Therapeutic Systems") discloses an arrangement in which air is prevented from entering the lungs until a prescribed threshold of vacuum is obtained by a user. Air is then abruptly permitted to flow to the lungs. This may be contradicted in a subject in shock or respiratory distress.

WO 1995/028192 ("Dura Pharmaceuticals") describes a dry powder medicine inhaler having a housing and a mouthpiece. An impeller is rotatably mounted on a pin to rotate within the aerosolizing chamber. Radial inlets pass through the housing and enter substantially tangentially into the chamber. A charging plunger is pressed downward in operation against the bias of a spring to press a full dose of powdered medicine into the chamber. The plunger is then held against the spring bias during operation and forms a top portion of the wall of the chamber. A dosage cartridge may be placed on pegs in an open area. A hold down lever is then pivoted to retain the cartridge and lock a mouthpiece in its operative position. A multi-dose medicine containing cartridge may be used. The impeller is driven at high speed by a motor. The impeller acts as a centrifugal air pump drawing air through the inlet and is driven by a high speed electric motor which relies on one or a pair of batteries. Again, this device relies on battery input. However, the device can be operated by inhalation from the user alone. The device does not appear to be environmentally sealed against moisture in particular. Further, in both embodiments, it is a relatively complex device and is restricted to use of powder.

WO 2000/018455 ("Glaxo") provides an inhalation device suitable for dispensing respiratory medication. It has a cover to prevent build-up of dust on the mouthpiece but is not sealed against water. It also has a geared and relatively complex actuator for use in operation.

WO 2002/004043 ("Vapotronics") discloses an inhaler to deliver medicament or other fluids in droplet form and during inhalation. The inhaler has an airflow conduit assembly extending through the housing, a mouthpiece which is fluidly interconnectable with the airflow conduit assembly and a droplet ejection cartridge housing. A droplet ejection is removably disposed within the cartridge housing. The airflow conduit assembly may include a plenum into which air is initially drawn. The mouthpiece is removable and stowable on the device. A droplet ejection cartridge is provided which includes a medicament reservoir, a plurality of droplet ejection orifices and at least one droplet ejection actuator. The droplet ejection cartridge includes a PCB interface on one of its sides for interfacing with a printed circuit board which controls the operation of the inhaler. Pressure sensors are used to activate the device and a nozzle region is provided which includes a plurality of droplet ejection orifices. Each droplet ejection orifice has its own resistor, such as there is a one-to-one relationship for dispensing the medicament. The device is therefore a complex electronic arrangement and relies on electric power in use. It may have limited application in harsh environments.

As noted, in inclement circumstances, the risk of contamination may be significant. A sealed, safe and robust storage arrangement would be of advantage, particularly if designed for easy and effective use when required.

Use of therapeutics in emergency situations may present different risks which can be highly serious. Delivery of an analgesic, for example, requires an arrangement that is robust, reliable and easy to operate. This is particularly the case in the circumstance of self-administration where a user may be, at least partially, incapacitated by injury or people lending assistance may be untrained in first aid.

Reference to any prior art in this specification is not, and should not be taken as, an acknowledgement or any form of suggestion that this prior art forms part of the common general knowledge in any country.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

In one aspect, the invention may reside in a portable medication holder for holding a medication container and discharging a liquid agent therefrom, the portable medication holder comprising a housing including a first wall forming a chamber of part thereof;

an air pathway passing through the chamber, a second wall engaging the first wall, and moveable between a closed position in which the chamber and air pathway are sealed and an open position in which the air pathway is open, evaporation means to assist in evaporation of the liquid agent into a medication discharge chute for directing the air pathway to a user; and opening means for opening the medication container and releasing the liquid agent to the evaporation means.

The device may include the medication container located in the chamber or in fluid communication with the chamber.

The medication container may be a vial, ampoule bottle or canister and is frangible, at least in part.

The liquid agent is preferably methoxyflurane.

The second wall may be formed as a cover or sleeve.

Preferably the opening means is automatically activated by moving the second wall to the open position.

The opening means may include a striker adapted to open the medication container.

The striker may be activated by sliding the second wall to the open position.

The opening means may include a punch to open a frangible seal in the container.

The opening means may include a seat to grip a cap, which may be a screw cap, of the container.

Alternatively or additionally, the opening means may include a plunger to pressurise and discharge the liquid agent.

The evaporation means may comprise a wick material.

Alternatively the evaporation means may comprise an evaporation plate or plates or a grid.

The evaporation means preferably forms a serpentine or tortuous path as part of the air pathway.

The medication chute is preferably rotatable between a stowed position and a deployed position.

The medication chute may further include a gas line for delivering a respiratory gas.

The medication chute may include an auxiliary air inlet adapted for complete or partial occlusion by a user.

The portable medication holder may include one or more one-way valves in the intake air pathway to provide unidirectional inspiratory airflow.

The medication chute is preferably in fluid connection with an outlet one-way valve for expired air.

The medication chute may be in fluid connection with a filter for removing medication from expired air.

Preferably the portable medication holder is sealed against the external environment when not in use.

The portable medication holder may include a strap, preferably a wrist strap attached to the second wall.

In one alternative form, although it need not be the only or indeed the broadest form, the invention resides in a medication holder, the medication holder comprising:

a housing including a first wall defining a cavity dimensioned to receive and enclose, at least in part, a medication container; and a second wall abutting the first wall and moveable relative thereto;

wherein:

the second wall may be moved reversibly between a first closed position to a second open position, the second open position providing or facilitating access to a medication discharge outlet of the medication container wherein the cavity is sealed against ingress of moisture or other contaminants when the second wall is in the closed position.

The medication holder may include a medication container positioned in the cavity.

Positioning of the second wall in the second open position preferably provides or clears an airflow pathway for inhalation and, optionally, expiration. The airflow pathway may include airflow control means such as one or more valves.

The first wall may be an inner wall. The second wall may be an outer wall in a sleeved relationship to the inner wall.

Preferably, the cavity sealingly encloses the medication container or that part within the cavity when the second wall is in the first closed position. "Abutting" includes both in direct contact and spaced by a sealing member or members. "Enclose, at least in part, the medication container" may include sealingly enclosing or enveloping the container through an encircling wall or a wall that abuts, preferably elastically, against a wall of the container to resist ingress of moisture or other contaminant.

The term "container" includes canisters, pressurized or otherwise, vials, capsules, blister packs, syringes and any other arrangement suitable for storage of medication and subsequent discharge in an embodiment of the present invention.

The housing may be formed from any suitable material, but is preferably formed from a durable polymer such as PVC, PEEK or PET or an alloy such as aluminium.

The housing is preferably formed of components that may be moulded or extruded.

The medication container may comprise a pressurized canister. The canister may be adapted to release a controlled dose of therapeutic agent. The canister may preferably contain multiple doses of the therapeutic agent. The medication container may be understood to include a mechanism that is pressurized or activated by the through flow of air inhaled by a user. This may include a rotatable impeller. The medication container may comprise a frangible container that is able to be ruptured to release the therapeutic agent. The container may be one or more ampoules which may be conveniently formed from glass or plastic. The container may comprise a sealed compartment containing the medication. The sealed compartment may have one or more frangible seals which, when broken, release medication to inhaled air. This sealed compartment may also be considered as a frangible container.

The first inner wall may define an enclosed bore dimensioned to receive the medication container. The first inner wall may be a continuous wall. The bore may be open at one or both ends. A first end region of the first inner wall adjacent a first opening may be adapted to engage a flexible membrane. The flexible membrane may be formed as a concertina-type membrane. The flexible membrane may be engageable with the first end region in a watertight or water-resistant manner and may also be airtight. The flexible membrane may be adapted for transferring a depressing force from a user's hand to the medication canister to activate it, when aligned for use. The flexible membrane may be formed as a thumb pad.

Alternatively, the first end region nay be formed as a closure of the bore. The closure may be operable to provide an airflow pathway through the bore. The closure may be twist operated and may be also adapted to advance a medication dose into position for inhaling.

The medication container may comprise a depot of medication and dispersal means for distributing the medication for ingestion or inhalation. The dispersal means may include a rotatable vane or impeller. The depot may comprise one or more capsules, each storing a dose of medication and arranged to rupture when in position for dispersal. The medication container may comprise an arrangement with an evaporation surface to facilitate evaporation of liquid such as a volatile material. The evaporation surface may be formed by an absorbent material or wick which is preferably arranged in one or more folds to increase the evaporation area. The evaporation surface may be formed by one or more panels forming a surface over which inhaled air flows. The evaporation surface may be formed as a grid. The evaporation surface may form a tortuous airflow pathway or a serpentine airflow pathway for inhaled air.

A second end region of the inner wall may abut or form a second end opening of the bore. The second end opening may be formed as a lateral aperture. The second end opening is preferably closed by the outer wall when in the tint closed position.

Preferably, the bore contains a mouthpiece which may be adapted to receive a dispensed dose of medication from the container which may be provided by a valve end of the canister. The mouthpiece may comprise a seat for receiving the canister and a medication channel adapted to direct a dose of medication in a desired direction. Alternatively, the mouthpiece may simply comprise the medication channel. The mouth piece may be formed as a simple airflow pathway.

Preferably, the mouthpiece is pivotally mounted and rotatable between a first stowed position and a second deployed position, wherein the medication channel is positioned to deliver medication to a user. The mouthpiece may be pivoted between the stowed and deployed positions manually. Preferably, the mouthpiece is biased towards the deployed position. The mouthpiece may be released by movement of the second wall to the second position. The mouthpiece may be urged to a stowed or deployed position by movement of the second wall in a first or second opposite direction, respectively. The mouthpiece may be biased towards the deployed position by spring means. The mouthpiece may include an air intake vent or gas supply outlet, the gas preferably being air or oxygen. Alternatively or additionally, the first and/or second side walls may include at least one air intake vent which is preferably sealed when not in use.

The inner wall may define an end region of the housing.

The inner wall preferably is dimensioned to provide a recess or recesses to hold one or more additional medication container. The one or more additional medication containers may be stored substantially parallel to the medication canister.

The outer wall is preferably moveable relative to the inner wall by sliding. The walls are therefore slidable relative to each other. The outer wall may be formed as a sleeve member for partially or completely encircling or enclosing the inner wall for at least a portion of the inner wall's length. Preferably, the outer wall is slidable into a closed position abutting the second end region of the housing and an open position in a direction away from the second end region. The outer wall may be removed from the inter wall during operation. Preferably, the outer wall remains attached to the inner wall during use. Most preferably, the outer wall remains in a sleeved, abutting position with the inner wall during use. The outer and inner walls may be circumferentially slidable relative to each other. The outer wall may be shrunk into sealing contact with the inner wall during manufacture.

The housing may include sealing means for enhancing a water-resistant seal between the outer and inner walls, particularly when the outer wall is in a closed position. The sealing means may comprise one or more seals, preferably O rings, positioned between or in either the outer wall or the inner wall, preferably in the outer wall.

The housing preferably further comprises attachment means for attaching the medication holder to an item such as a sports bag or, preferably, to a user. The attachment means may be am eye and strap arrangement for positioning the device around the neck of a user or around a portion of a sports bag or similar.

Preferably, the attachment means is a band adapted for positioning around the limb of a user or around a strap of a bag or similar. The band is preferably a wristband. The medication holder may be attached to the wristband in any suitable fashion. In one basic form, the band may be required to be removed for use of the medication holder.

Preferably, however, the housing is fixed to the band by a pivot fitting which permits the housing to be rotated between a first storage position and a second use position. The first storage position may be substantially aligned with the longitudinal axis of a user's limb such as an arm and the second use position may be substantially transverse to the longitudinal axis and thereby accessible for easy use.

The band may be fixed by any standard means, such as a buckle or Velcro strap. The band may be elasticized. The band may further incorporate other items such as a diving watch, stopwatch, alarm or other items sometimes required during outdoor and sporting activities.

Alternatively, the housing may be fixed to a clip in a demountable manner, the clip adapted to engage a support item. The support item may be a belt, band, strap, waistband, pocket, soldier's backpack and/or webbing, utility belt or similar. The housing may engage the clip though a snapfit connector.

In a further aspect, the invention may reside in a housing for use in a medication holder, the housing substantially as described above.

In another aspect, the invention resides in a medication holder for a medication container having a housing, the housing comprising:

a first wall defining a cavity dimensioned to receive and enclose, at least in part, the medication container; and a second wall engaging or abutting the first wall and moveable relative thereto;

wherein the second wall is connected to the first wall and adapted to move between a first closed position and a second open position providing access to a medication discharge outlet of the medication canister or arrangement. The medication holder may include the medication container.

The medication container may comprise a frangible ampoule or vial and may further include an evaporation surface. The evaporation surface may be formed by a material wick or element or an increased surface area such as a grid. The frangible ampoule or vial may be ruptured by movement of the second wall between the first closed position and the second open position. Additionally or alternatively, the medication container may comprise a compartment containing the medication and one or more frangible seals in the compartment wherein rupture of the one or more seals introduces medication into an airstream. The frangible ampoule, vial or seal may be ruptured by a mechanically operated actuator. The actuator may be a plunger or a digitally operated button. The actuator may be activated by sliding movement of the walls relative to each other and preferably movement of the first wall to the second open position.

The second wall may be connected to the first wall by a tether arrangement. Preferably, the second wall is connected to the first wall by a pivot arrangement. The second wall may be slideably engaged with the first wall.

The frangible vial may be engaged via a cap with a screw thread. The cap may be mateable with a seat in the housing for fixation while the vial is separated and subsequently urged into a dispensing compartment to discharge its contents.

In another aspect, the invention resides in a medication holder for storing and dispensing a therapeutic agent, the medication holder comprising a housing including an inner wall forming a cavity configured as a bore, an outer wall formed as a sleeve to encircle the first wall for at least a portion of its length, actuator means for actuating dispensing of the therapeutic agent, the actuator means sealing one end of the cavity, a pressurized container housing the therapeutic agent and positioned in the cavity, and a medication chute moveable between a stowed position and a deployed position, wherein the first wall and second wall co-operate to seal the cavity to resist ingress of moisture and other contaminants and the second wall is slidable relative to the first wall to provide access to and facilitate deployment of the medication chute.

The second wall may be slidable longitudinally and remain in contact with the first wall.

The second wall may slide circumferentially to the open position.

Sliding of the second wall may drive a rack and pinion arrangement to move the medication chute linearly between the stowed and deployed positions.

The actuator means may be a pressure pad for urging the medication canister downwardly against a discharge seat.

The actuator means may be a twist-top arrangement for activating a cam mechanism to displace the medication canister against the discharge seat.

Activation of the actuator means may open an air pathway through the cavity.

In a further aspect, the invention resides in a portable medication holder for holding and discharging a medication container holding a liquid agent, the portable medication holder comprising a housing including a first wall forming a chamber, an air pathway passing through the chamber, a second wall engaging the first wall, the second wall formed as a sleeve located around the first wall, the second wall moveable between a closed position in which the chamber and air pathway are sealed and an open position in the air pathway is open, evaporation means to assist in evaporation of the liquid agent into air in the air pathway, a medication discharge chute for directing the air pathway to a user, opening means for opening the medication container, and the medication container located in the chamber or in fluid communication with the chamber.

The medication container may be a vial, ampoule or canister and is frangible, at least in part and may store methoxyfluorane.

The second wall may be formed as a cover and the opening means may include a striker adapted to open the medication container.

The striker is optionally activated by sliding the second wall to the open position.

Alternatively or additionally, the opening means may include a punch to open a frangible seal in the container.

The opening means may include a seat to grip a screw cap or a bottle.

The evaporation means may comprise a wick material or the evaporation means may comprise an evaporation plate or plates or a grid.

The evaporation means may provide a serpentine or tortuous path as part of the air pathway.

The medication chute may be rotatable between a stowed position and a deployed position.

The medication chute may include a gas line for delivering a respiratory gas.

The medication chute may include an auxiliary air inlet.

The medication chute may also include one or more one-way valves in the intake air pathway to provide unidirectional inspiratory airflow and/or a one-way valve for expiratory air.

The medication chute may be in fluid connection with a filter for removing medication from expired air.

In a further aspect, the housing may include a support engageable with a strap, belt, item of clothing or similar. The support may be demountable from the other housing components.

BRIEF DESCRIPTION OF THE DRAWINGS

In order to provide a better understanding of the present invention, preferred embodiments will be described in detail, by way of example only, with reference to the accompanying drawings in which:

FIG. 18 is a perspective view of a further embodiment of a medication holder adapted for attachment to a strap or similar;

FIGS. 33A-33C is a series of views of still another medication holder of the present invention;

FIGS. 35A-35B shows two perspective views of part of a counting or indicating arrangement in a housing of the present invention;

DETAILED DESCRIPTION OF THE DRAWINGS

Figure 1:
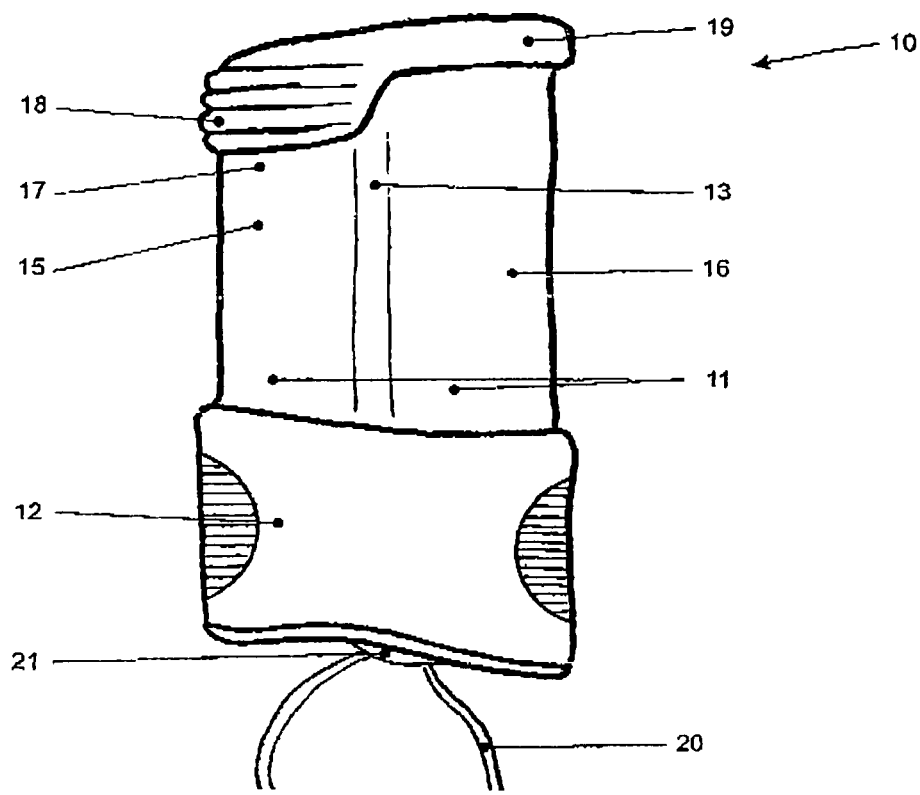
FIG. 1 is a front view of a first embodiment of a medication holder incorporating a spare medication canister.

Referring to FIG. 1, there is seen a medication holder which in this case is exemplified by a housing 10 comprising an inner wall 11 and outer wall 12.

Figure 8:
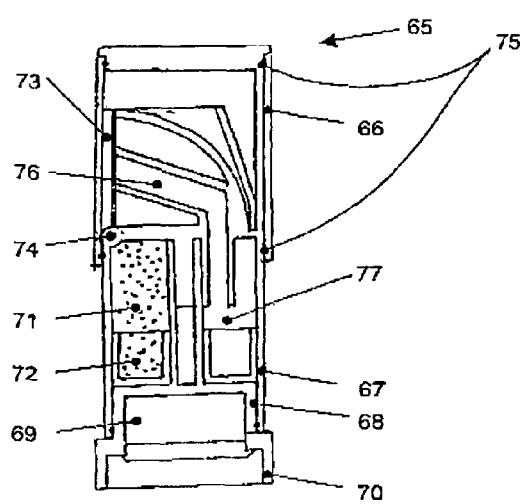
FIG. 8 is a side sectional view of a further embodiment of a medication holder.

The inner wall 11 is formed as a continuous wall and is substantially in the shape of a FIG. 8 arrangement in cross-section. An intermediate recess 13 defines the border between a cavity or chamber in the form of a first active bore 15 and second storage bore 16.

A first end region 17 of the active bore 15 is capped with the flexible membrane 18, which may also extend across the end of the storage bore 16 to thereby seal both bores. The storage bore 16 may be capped by a separate cap 19 to provide independent operation of the two capping mechanisms. However, in general, it is envisaged that the end capping arrangement would be continuous to allow easy removal and positioning of a fresh canister in the active bore 15 with subsequent recapping for use. It should be noted, however, that the device may be able to be used without the end cap at all. The wall of the first bore 15 may be attached to a flexible skirt-like structure (not shown) with an aperture for receiving and snugly adjoining the wall of a medication container such as a canister. A resilient diaphragm may be positioned in the bore to sealingly engage the wall of a canister to thereby isolate the mouthpiece and render it waterproof.

In some embodiments, the medication container may comprise an arrangement for delivering a solid therapeutic agent, such as in powdered form, or indeed a liquid therapeutic agent. In this case, it may be desired to have a through bore which is patent and allows the inspiration of air flowing through the bore and canister arrangement to activate a spinhaler or similar and disperse a therapeutic agent. The through bore may also be provided for use with a pressurized canister. The spinhaler may be provided with powder carried in a separate capsule or similar arrangement. The capsule may be mounted in a seat in the bore and pierced to release powder for subsequent inhalation. In this case, the storage bore may in fact be adapted to store solid medication, preferably in the form of powder. The powder may be in individual doses formed in gelatin capsules or similar. Alternatively, the powder may be provided as a bulk quantity with a measuring spoon for loading into the active bore. The term "medication container" therefore can be viewed as extending to these arrangements which provide a means of medicating an airstream delivered to the mouth or nose. The through bore may be usually closed and only opened during operation of the device, thereby sealing the medication holder or housing when not in use.

In this embodiment, a neck strap 20 is shown mounted to a receiving eye 21. The neck strap allows the positioning of the housing 10 around the neck of a user. In the subsequent discussion, it will be seen that a user may simply slide the outer wall 12 into an open position with the holder inverted for immediate and easy use.

Figure 2:
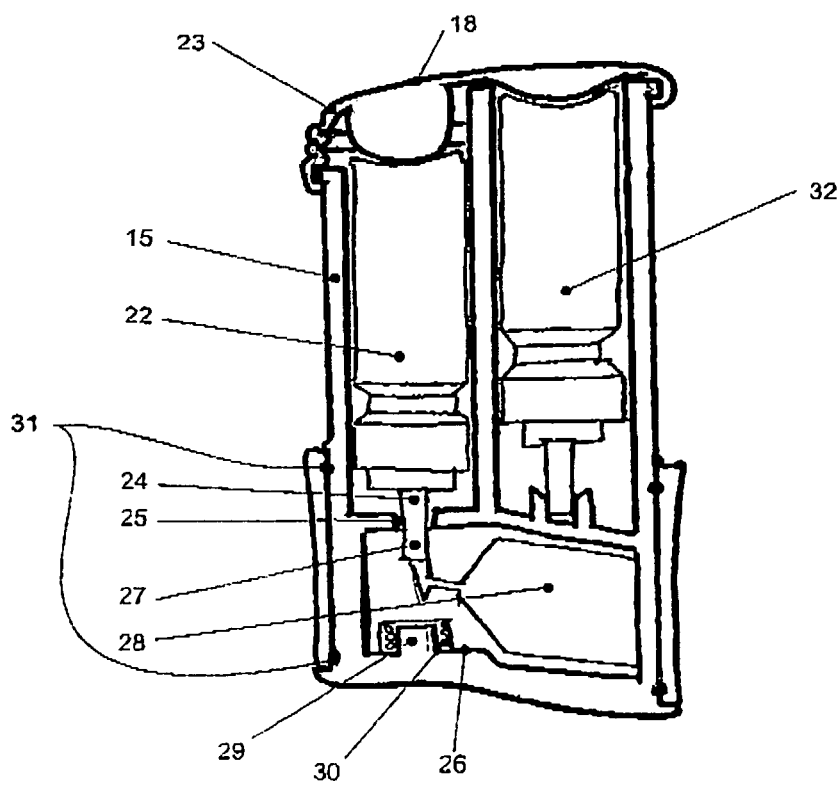
FIG. 2 is a sectional view of the arrangement of FIG. 1.

The internal arrangement of the device of FIG. 1 can be seen in FIG. 2. A medication container in the form of first pressurized metered dose inhaler 22 is positioned in the active bore 15.

The flexible membrane in the form of a cover cap 18 is seen to be an integral unit which sits above an activation button 23. The canister 22 has a valve stem 24 positioned in a seat 25 in a cap or mouthpiece 26. The term "mouthpiece" may also include a nosepiece. The valve stem has a discharge channel 27 leading to a discharge aperture 28 in the mouthpiece or cap 26. The mouthpiece 26 is pivotally mounted on stud 29 and tensioned by a spring 30. The spring 30 biases the mouthpiece into a deployed position. O ring seals 31 are provided to resist the ingress of moisture and other contaminants. The presence of the seals is beneficial as it lends great utility and robustness to the holder and enhances suitability for use in wet environments, in forest and bush settings, in mud and around dust and other potentially dangerous environmental features. The seals are located between the two walls and may be formed of any suitable polymer such as rubber or silicon-based material. Preferably, the seals provide a limited resistance to the sliding of the outer wall 12 over the inner wall 11.

A spare canister 32 is seen in position. The canister may contain the same agent as the pressurized dose canister 22. Alternatively, the canister may contain a different therapeutic agent, thus allowing the holder to provide alternative forms of medication. It is also clear that the holder may be designed to carry two or more spare canisters, each being a duplicate or a source of an alternative therapeutic agent.

Figure 3:
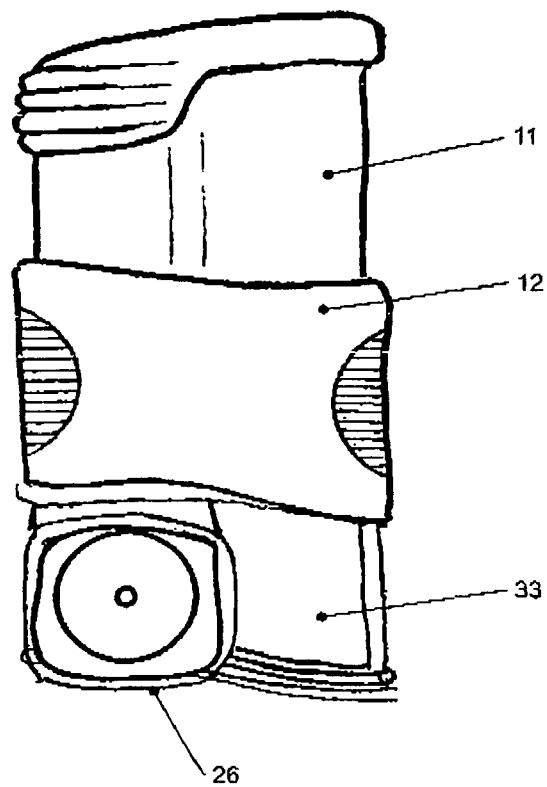
FIG. 3 is a front view of the arrangement of FIG. 1 when deployed for use.

FIG. 3 shows a front view of the arrangement of FIG. 1 with the outer wall 12 slid into its open position, thereby clearing the bore containing the canister. The bore also provides space 33 for location of the mouthpiece 26 when in rotated stored position.

The mouthpiece 26 is directed outwardly of the medication holder and positioned for easy access by a user after rotation around a longitudinal axis. The mouthpiece may include an air intake vent or vents (not shown) to provide inhalation air when a user places his or her lips on the mouthpiece. The mouthpiece may comprise the seat 25 and medication channel formed as the discharge chute.

Figure 4:
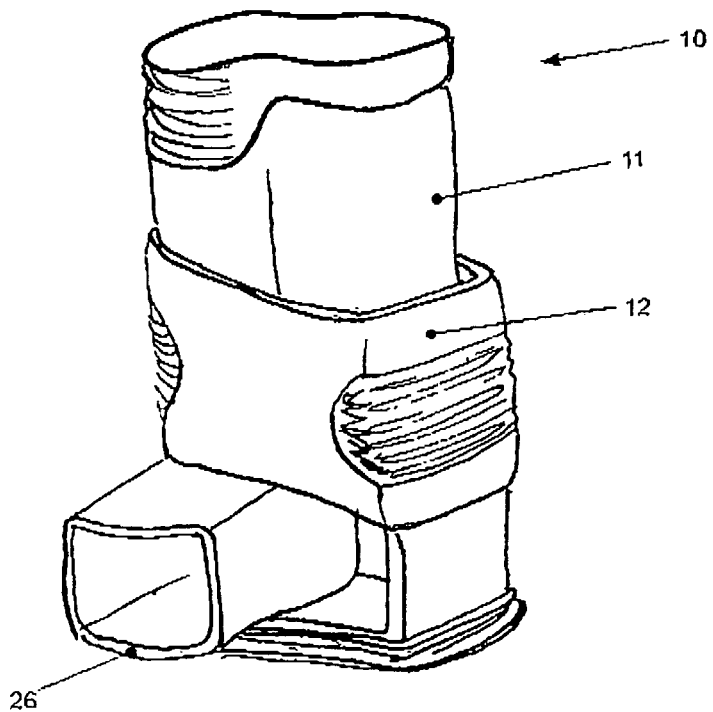
FIG. 4 is a perspective view of the arrangement of FIG. 3.

FIG. 4 provides a further perspective view of this arrangement.

Figure 5:
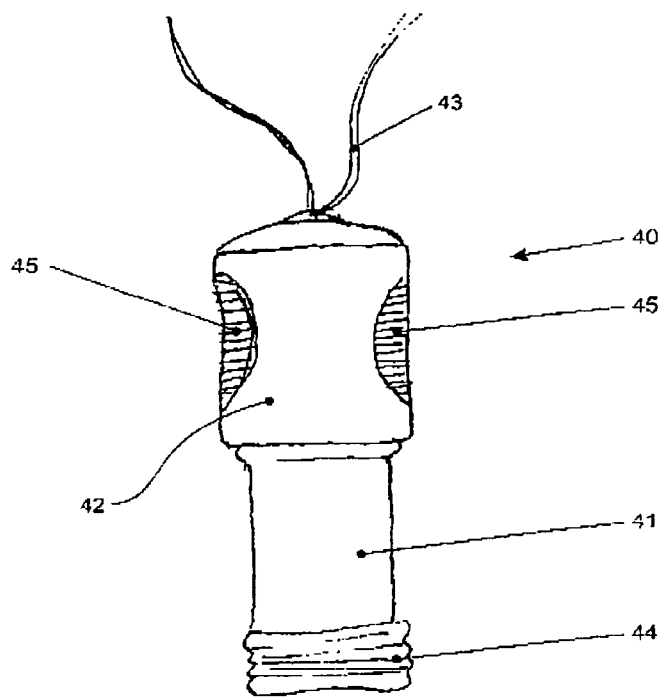
FIG. 5 is a front view of a second embodiment of a medication holder for a single medication container.

FIG. 5 shows an embodiment in which a single canister is installed in the medication holder 40. An inner wall 41 is surrounded by an outer wall sleeve 42 for a portion of its longitudinal length. This, embodiment again has a neck strap 43. It also has a concertina-like flexible membrane cap 44 on a first end of the inner wall 41.

While it is generally preferred that the inner and outer walls are formed from the same material, it is possible to use different materials for each of the components. The walls may be formed from lightweight durable polymers but could also be formed of metal. The outer wall 42 is shown with grip-enhancing pads 45 to facilitate use.

While emphasis has been placed on the use of therapeutic agents, it is also clear that the medication holder may store non-medical agents such as vitamin supplements, energy-boosting substances, electrolyte replacements and similar. One example of such a material may be glucose for diabetes sufferers for use in the event of a hypoglycaemic episode. Simple application of glucose may be sufficient to raise the blood glucose levels and prevent the risk of hypoglycaemic sips including the life-threatening possibility of a hypoglycaemic coma. While such a person would clearly be suffering from a disease condition, the use of glucose in endurance athletes or for athletes in extreme conditions may be of considerable advantage in maintaining their homeostasis and circulatory equilibrium in an otherwise fit and pathology-free person. The medication may be directed to gastrointestinal absorption as opposed to or as well as respiratory tract targeting. Medication of the airstream should be understood to include for the purposes of gastrointestinal absorption as well as pulmonary delivery. Reference to "inhalation" may also refer therefore to gastrointestinal absorption, particularly through the mucous membrane of the upper gastrointestinal tract.

Figure 6:
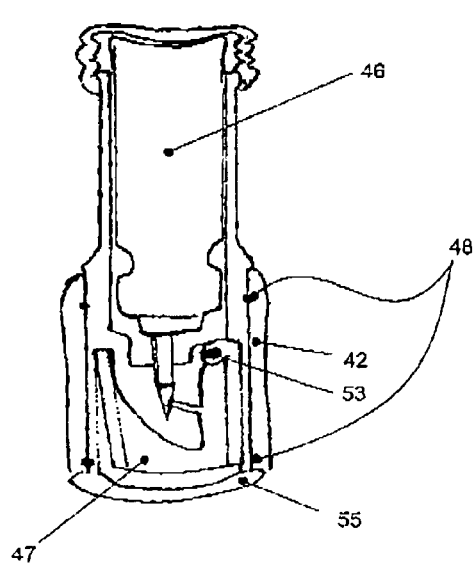
FIG. 6 is a sectional view of the arrangement of FIG. 5 when inverted for use.

FIG. 6 shows the arrangement of FIG. 5 inverted and in a stowed position. The canister 46 is apparent, as is the mouthpiece 47 and O ring seals 48.

Figure 7:
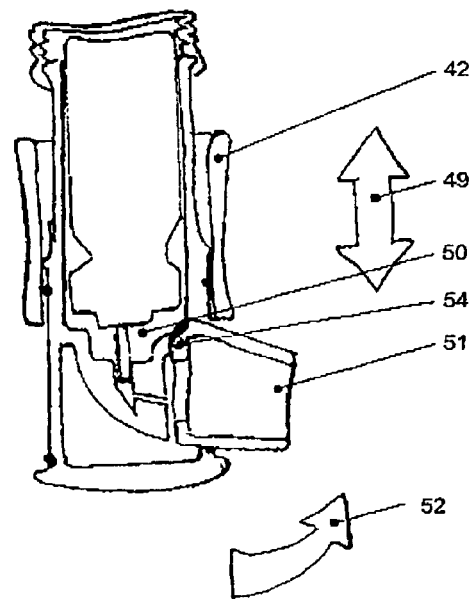
FIG. 7 is a sectional view of the arrangement of FIG. 6 when deployed for use.

In FIG. 7, the outer wall 42 has been slid in the upward direction of arrow 49 (i.e. longitudinally), cleared the bore 50 and allowed the mouthpiece 51 to pivot in the direction of arrow 52. This time, pivoting is in a front-to-back direction around pivot pin 53 (i.e. a transverse axis) and under the effect of spring 54. The holder 40 therefore does not require lateral storage space in the bore and allows storage of the mouthpiece in an up and down bore under the end or top region 55.

An alternative embodiment is shown in FIG. 8 in which the housing is exemplified by a medication holder 65 having an outer wall 66 and inner wall 67, the latter inner wall 67 forming a bore 68. A wad of moisture absorbing material 69 is placed in the bore next to an end twist base 70. A dry powder reservoir 71 is provided which is formed by a concentration of medication material. A secondary reservoir 72 contains a single dose of the powder and is refilled from the reservoir 71. A mouthpiece 73 is stowed by rotation around pivot point 74 with the outer wall 66 positioned to retain it in a retracted location as shown. O ring seals 75 provide a barrier to ingress of unwanted materials. An airflow pathway or flow path 76 is formed to lead away from an inhalation area 77.

Figure 9:
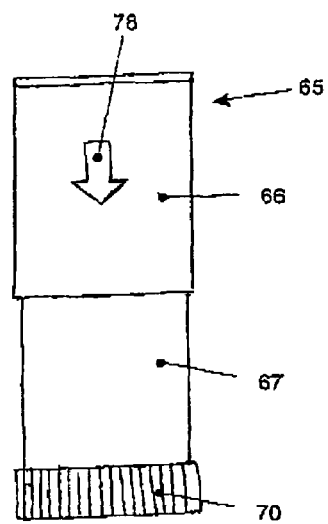
FIG. 9 is a side view of the medication holder of FIG. 8.

FIG. 9 shows a view of the device 65 with an arrow 78 indicating the direction in which the outer wall 66 will slide relative to the inner wall in operation. It is within the concept of the invention to reverse the inner and outer walls and have the inner wall slide inside the outer wall to release the mouthpiece. The walls therefore move relative to each other.

Figure 10:
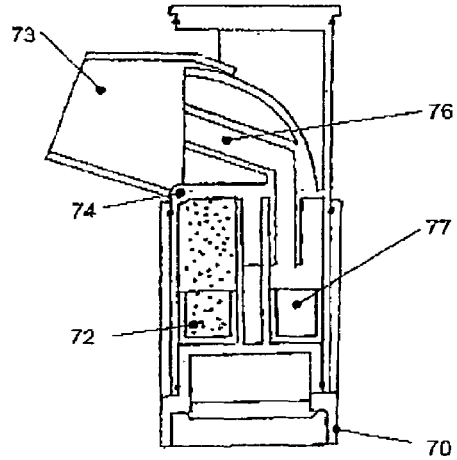
FIG. 10 is a side sectional view of the arrangement of FIG. 8 when deployed for use.

FIG. 10 shows the mouthpiece 73 rotated around the pivot point 74 and in working position relative to the flow path 76. The end twist base 70 may be rotated to move the dose in the secondary reservoir 72 into the inhalation area 77. Rotation of the twist base 70 opens and creates a patent air pathway from the twist base 70 through to the mouthpiece 73. A user may then inhale through the mouthpiece 73 pulling air through the device and entraining the powdered medication for subsequent inhalation or absorption. Further doses of the compound may be provided by additional twisting of the twist base, preferably in a reciprocating action.

Figure 11:
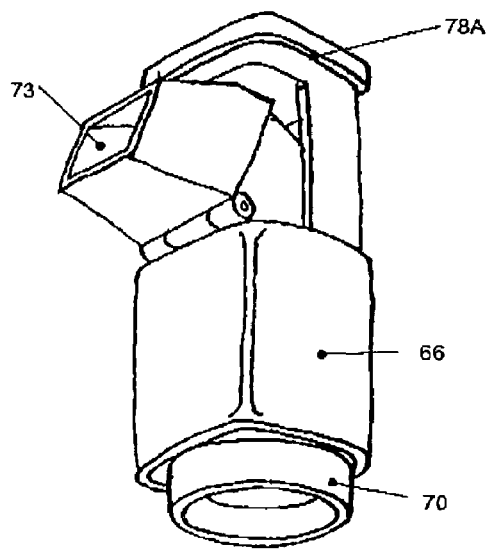
FIG. 11 is a perspective view of the configuration of FIG. 10.

FIG. 11 shows the components as seen in a perspective. In this case, the twist base forms a closure but when activated provides a patent air path through the device. An end section 78A acts as a top cap for the medication holder, which also closes one end of the bore.

Figures 12, 13, 14:
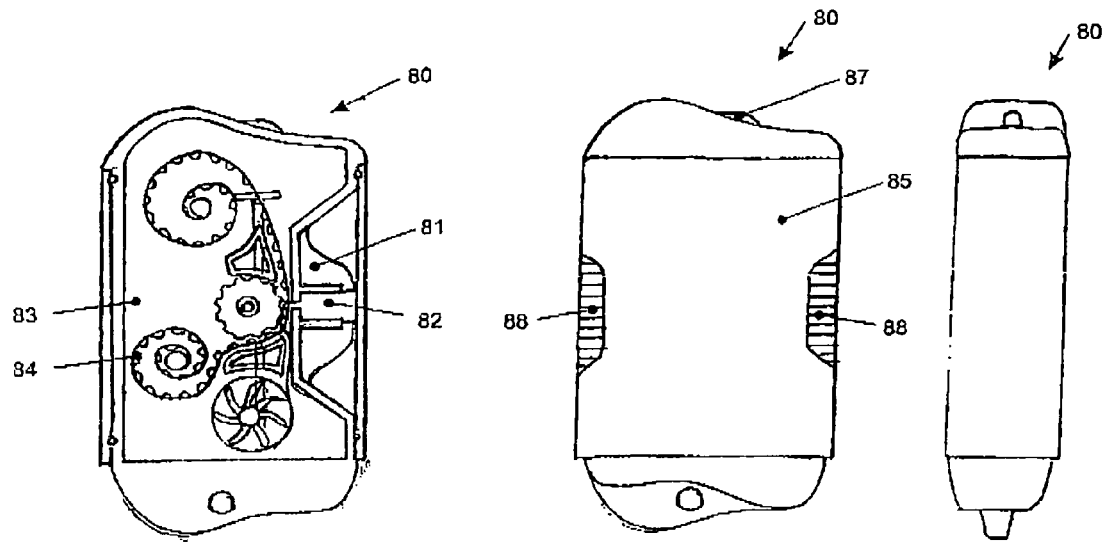
FIG. 12 is a sectional view of yet another embodiment of a medication holder.
FIG. 13 is a front view of the medication holder of FIG. 12.
FIG. 14 is a side view of the medication holder of FIG. 13.

A cross section of yet a further embodiment of a housing is shown in FIG. 12 in which a medication holder 80 is seen in side sectional view. The medication holder 80 has a mouthpiece 81 and drug delivery point 82.

A geared arrangement shown generally as 83 is configured to operate a blister pack roll 84 formed of a flexible backing material with blister packs containing predetermined doses of medication. Operation of the geared arrangement 83 may be through the action of sliding outer wall 85 over the inner wall 86 thereby causing rotation of the gears, advancement of the blister pack roll 84 and rupture of one blister pack at the drag delivery point 82 to present the medication for inhalation. The device may be provided with a neck strap attachment 87.

FIG. 13 shows the device in side view with finger grips 88 apparent.

FIG. 14 shows the slim line nature of the device which allows it to be formed as an easily carried and unobtrusive but fully closed package.

Figure 15:
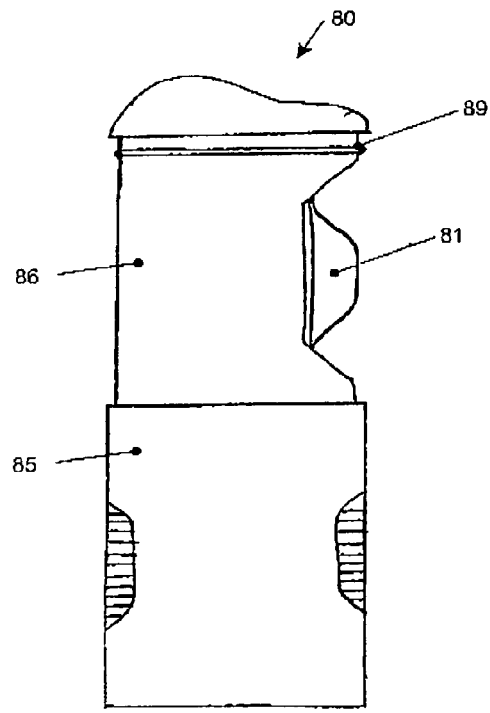
FIG. 15 shows the medication holder of FIG. 13 when ready for use.

FIG. 15 shows the medical holder 80 with outer side wall 85 slid out of alignment with an O-ring seal 89 thereby exposing the mouthpiece 81 allowing a user to access it and inhale the medication provided from the ruptured blister pack. Movement of the wall 85 both advances the blister pack roll as well as clearing an aperture to permit through flow of air once a user inhales while engaging the mouthpiece.

Figure 16:
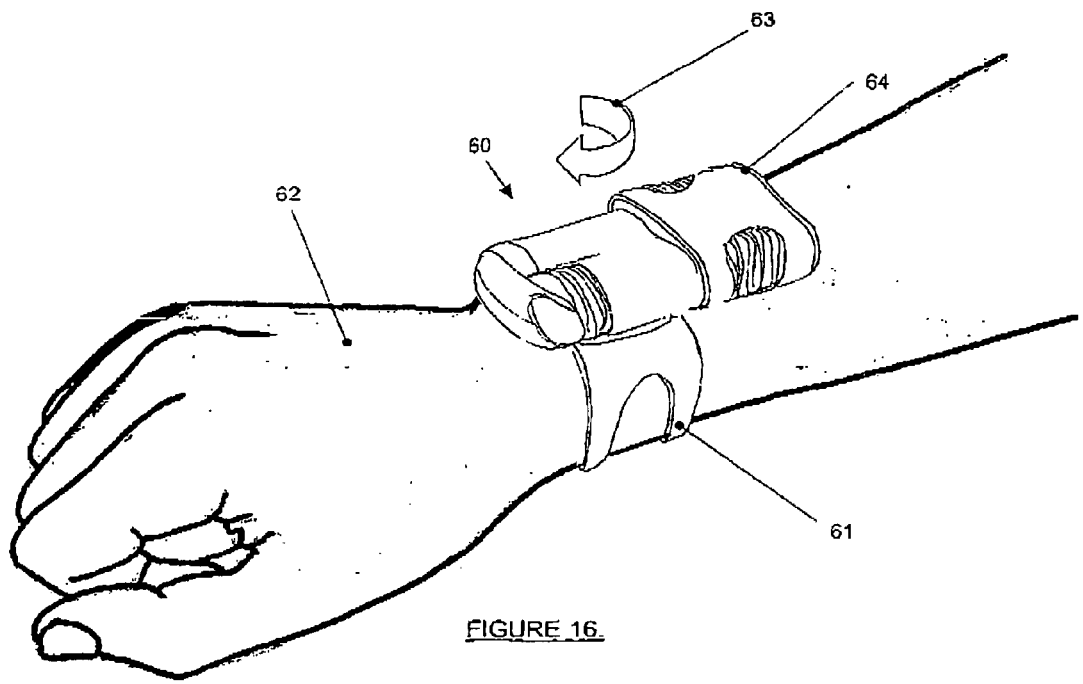
FIG. 16 is a preferred embodiment of the arrangement of FIG. 2 when adapted for mounting to a wristband.

FIG. 16 shows a preferred embodiment in which a medication holder 60 is rotatably mounted to a wristband 61, in turn, mounted on the arm 62 of a user. The holder may be rotated in the direction of arrow 63 for deployment for use. When not in use, the longitudinal axis of the holder 60 is substantially parallel with that of the arm 62, thereby providing a neat and non-extruding profile when being carried by a user. When required, the holder 60 may be rotated through 90° and the outer wall 64 slid clear of the aperture leading to rotation and presentation of the mouthpiece (not shown). In this orientation, a user may simply bring his or her forearm up to alignment with the user's mouth or nose. In this case, the outer wall 64 may have a slotted underside to allow movement relative to the pivotal mounting. Once used, the outer wall 64 may be then slid back into a closed position and the holder rotated back through 90° for its carriage position. The method of attachment to the wristband may be any suitable arrangement such as friction plates or rotation plates with indentations for preferred positioning.

While a straightforward band 61 is shown in this view, it is clear that mounting arrangements may be fixed to other items commonly worn on the wrist such as watches, depth gauges, stopwatches, altimeters and heart rate monitors.

Figure 17:
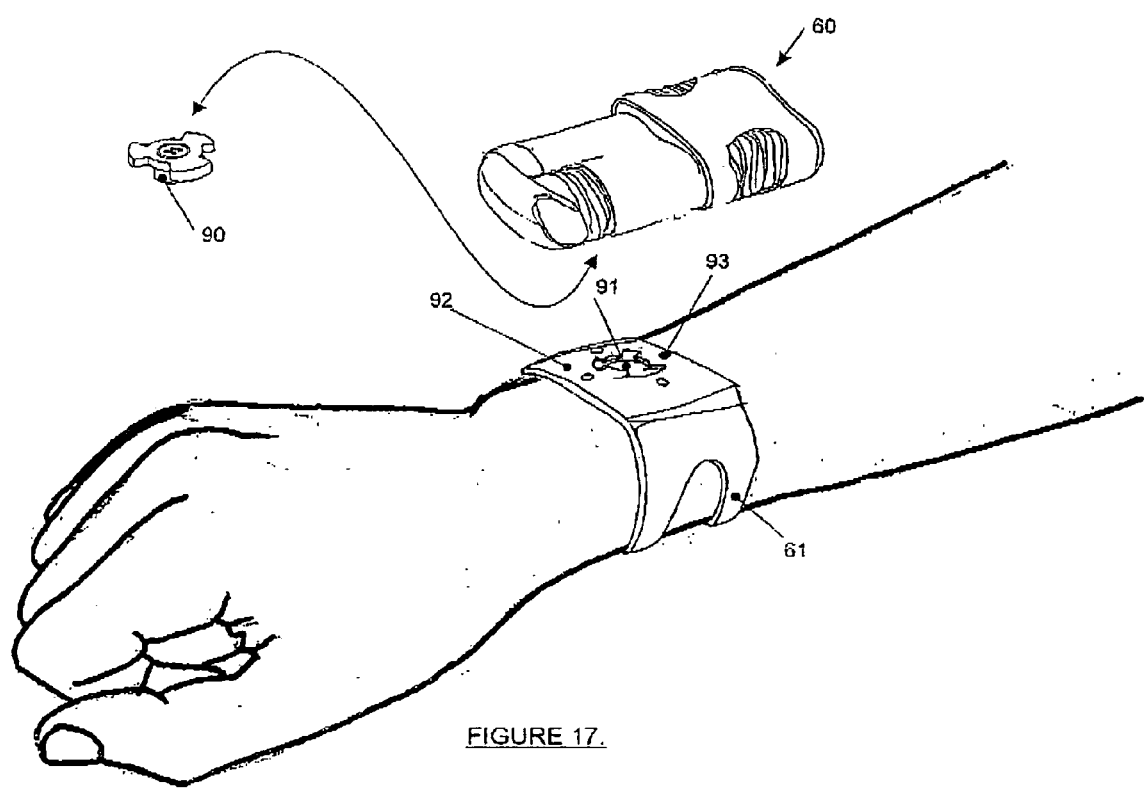
FIG. 17 is an exploded view of the arrangement of FIG. 16.

The arrangement of FIG. 16 is shown in exploded view in FIG. 17 of the medication holder 60 coupled to a wrist mount attachment 90 which in turn fits into a seat 91 on a plate 92 which is continuous with wristband 61. Small lugs 93 act as stops to resist rotation. Use of appropriate rotational force will overcome this resistance and cause the medication holder to rise up and rotate through 90° to the next lug. Additional force may keep the device rotating but it is envisaged that a range of 90° will be adequate to discharge the function of the device.

The present invention provides a considerable number of advantages. A medication source may be easily and conveniently carried by a person in virtually any circumstance. A preferred circumstance is in the sporting or outdoor arena where the medication holder may be formed as a substantially waterproof item with robust and hardwearing characteristics that make it difficult to damage while providing easy and instant access to a hygienic and ready-to-use medication source. Many people with asthma or other conditions have a degree of embarrassment about the use of inhalers and similar and in publicly displaying their canisters. The present invention provides an effective way of carrying the canister in a fashionable and stylish way which may address at least some of this inhibition. The housing may be provided in a colored arrangement with or without advertising indicia and may be labeled with information on the drug housed within. They may be provided by sports promoters or pharmaceutical companies as well as made available for private purchase. The medication holder may be used in sports in a wide range of terrains and, in fact, in any terrain or environment that is accessible by a participant. Carrying or wearing the medication canister or even locating it in association with a carried item or object will lead to minimal or no interference with performance by an athlete.

While the emphasis is on sports use, it is also clear that any potential user of a medication carried in a canister may find a reason for and advantage in using the present housing.

Figure 18:
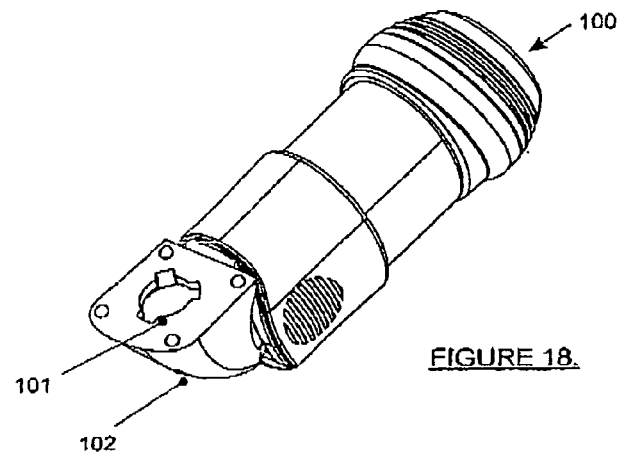
Figure 19:
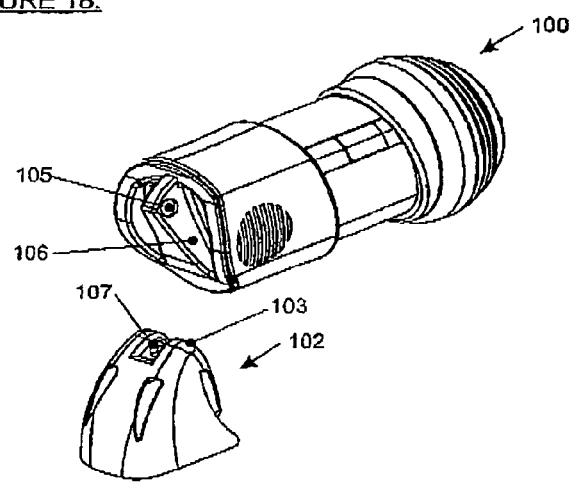
FIG. 19 is an exploded view of the medication holder of FIG. 18 in use.
Figure 19:
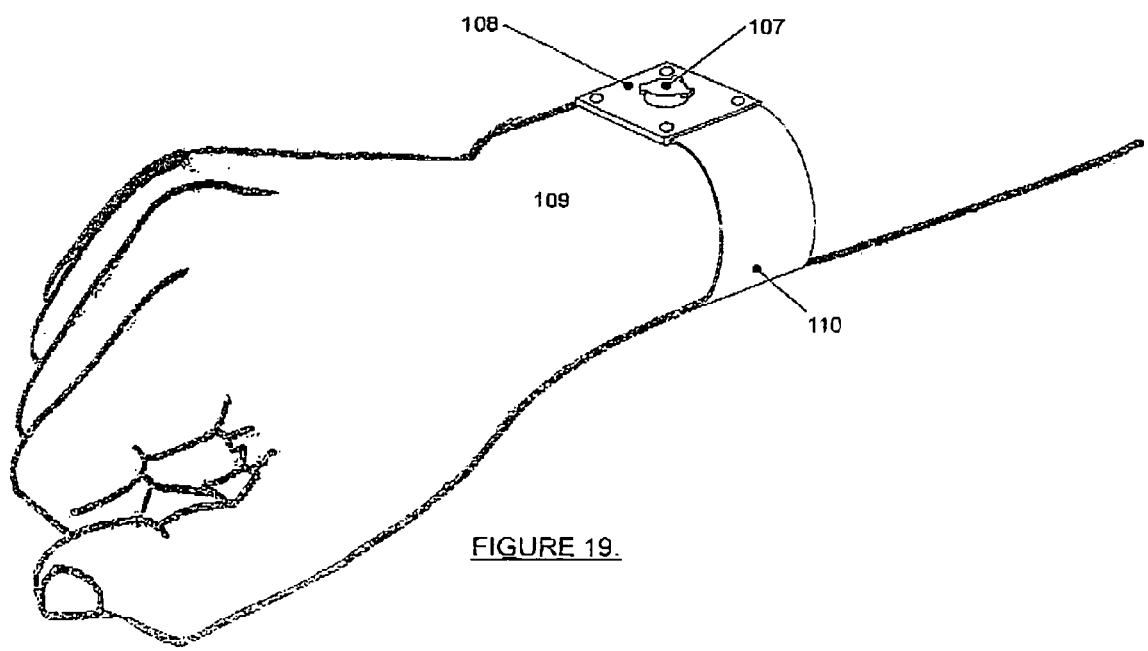

Referring to FIG. 18, there is seen an embodiment of a medication holder 100 which incorporates a locking recess 101 in a housing support 102 which is formed in a roughly triangular fashion terminating in a top ridge 103. The top ridge 103 has a recess 104. The recess 104 has a stud adapted to mount into a dimple 105 formed in a fin 106 on the top of the housing 100.

This arrangement allows rotation of the medication holder 100 relative to the support 102. The support in turn is mountable onto spigot 107 formed on base plate 108 mounted to the wrist 109 of a user by strap 110.

Figure 20:
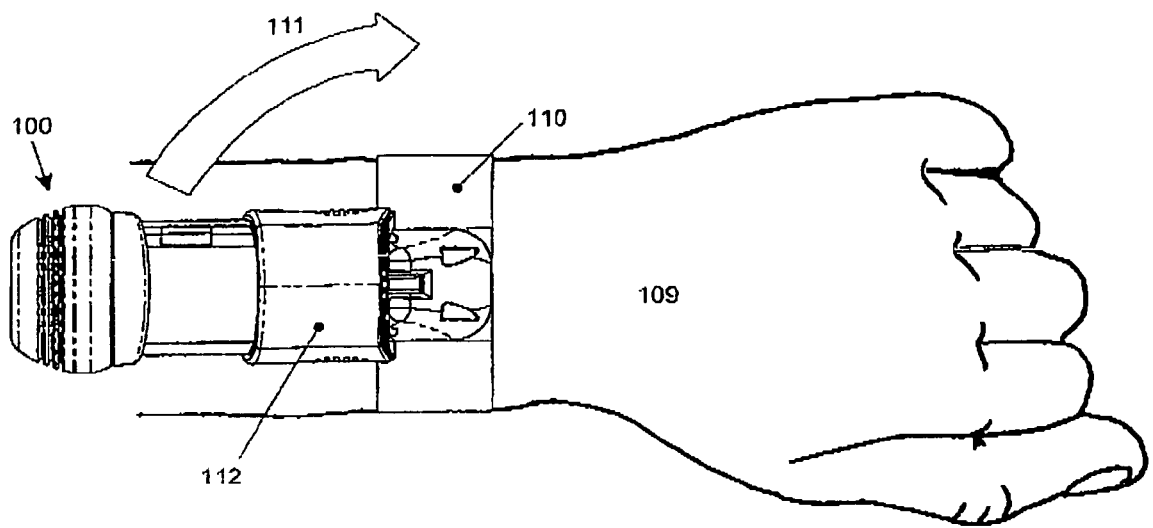
FIGS. 20 and 21 show the operation of the medication holder of FIG. 18.
Figure 21:
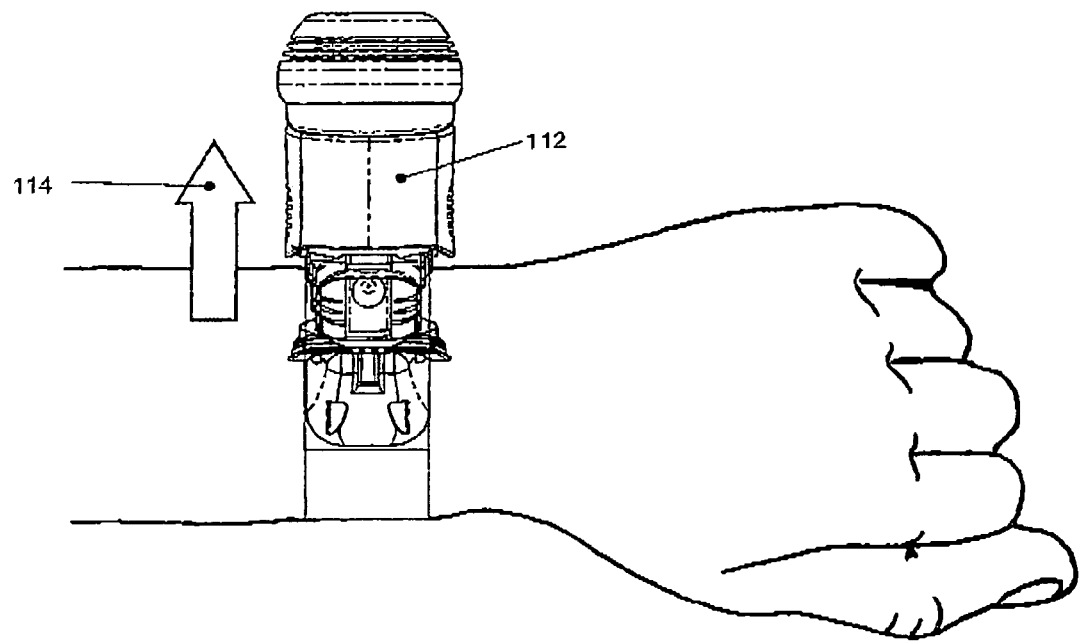

In FIG. 20, the medication holder 100 is aligned along a user's arm and fixed to the strap 110. It is therefore easily and safely carried with little opportunity to inhibit the user in his or her usual activities. When required for use, the holder 100 may be pivoted in the direction of arrow 111 to the position shown in FIG. 21. The outer wall 112 may then be slid in the direction of arrow 114 to expose the operative components including the mouthpiece. A medicated dosage inhaler may be depressed to eject a therapeutic substance into a user's mouth or nose while raising the wrist to place the chute in an effective position.

Figure 22:
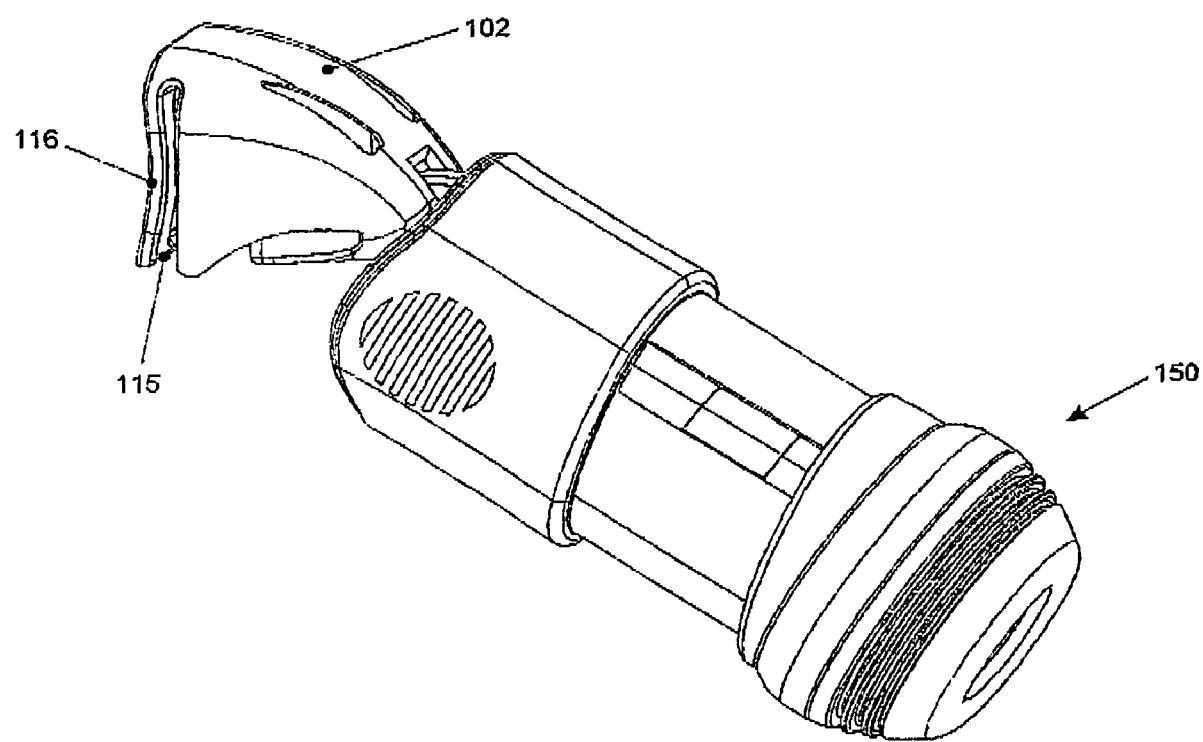
FIG. 22 is a perspective view of a further embodiment of a medication holder.

FIG. 22 shows a perspective view of a similar arrangement in which the medication holder 150 may be rotated relative to the support 102 and may even simply be disconnected from the support for easier use. In this case, the support does not have a locking recess but rather has a slot 115 formed by a resilient flap 116 and dimensioned for easy location over a strap, belt, the edge of a pocket, top of a shirt or similar.

Figure 23:
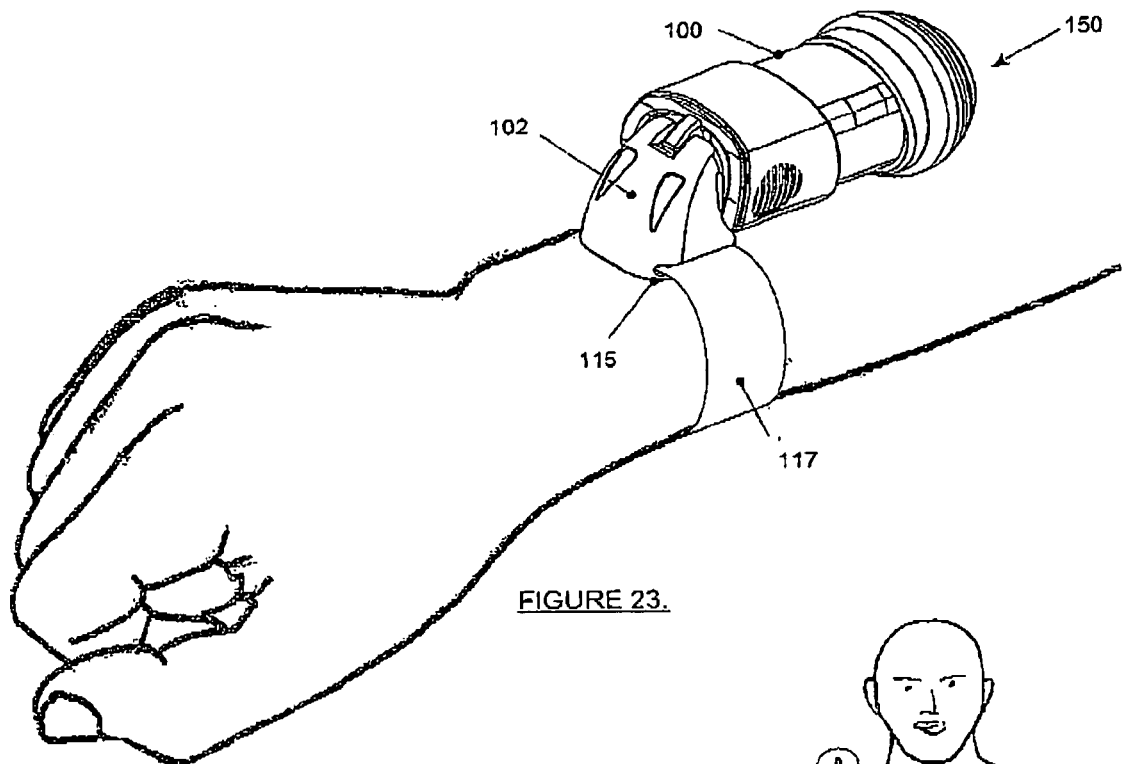
FIG. 23 is a view of the medication holder of FIG. 22 in position on a user's arm.

The operation of the embodiment of FIG. 22 is shown in FIG. 23 where the slot 115 is slipped onto the strap 117 and the medication housing 100 is held in position. In use, the medication holder 150 may simply be rotated away from the support 102 and disengaged. After use, it may then be snapped back into position.

Figure 24:
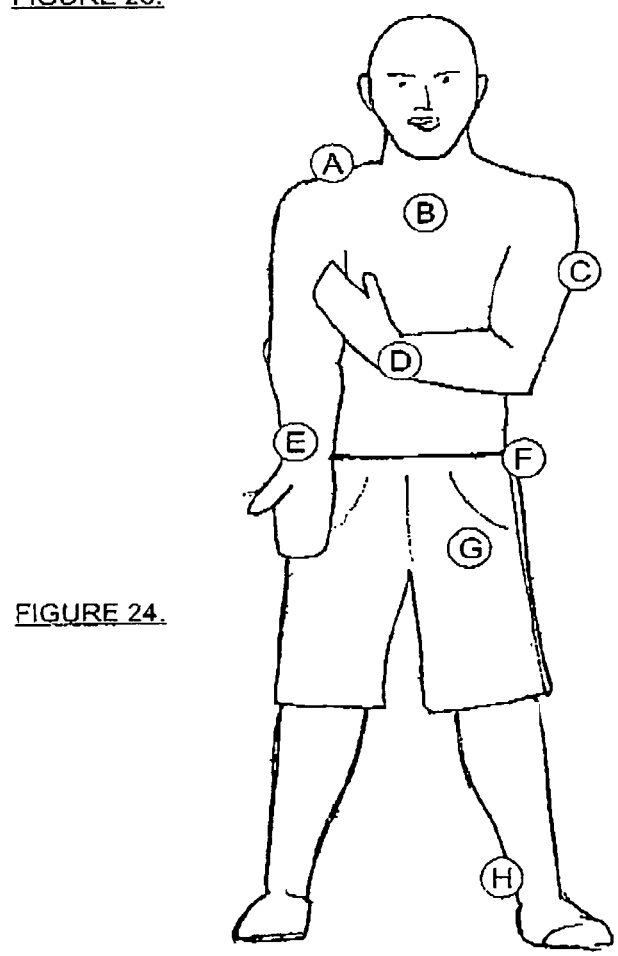
FIG. 24 is a schematic view of possible positions for the medication holder on the body of a user.

A wide range of positions may be used as shown in FIG. 24 and represented by letters. Representative positioning includes the shoulder A, around the neck or chest B, on an upper arm C, on top of the wrist D, under the wrist E, on a belt or waistband F, in a pocket G or on clothing or around the ankle H. Other positions may also be suitable.

Figure 25:
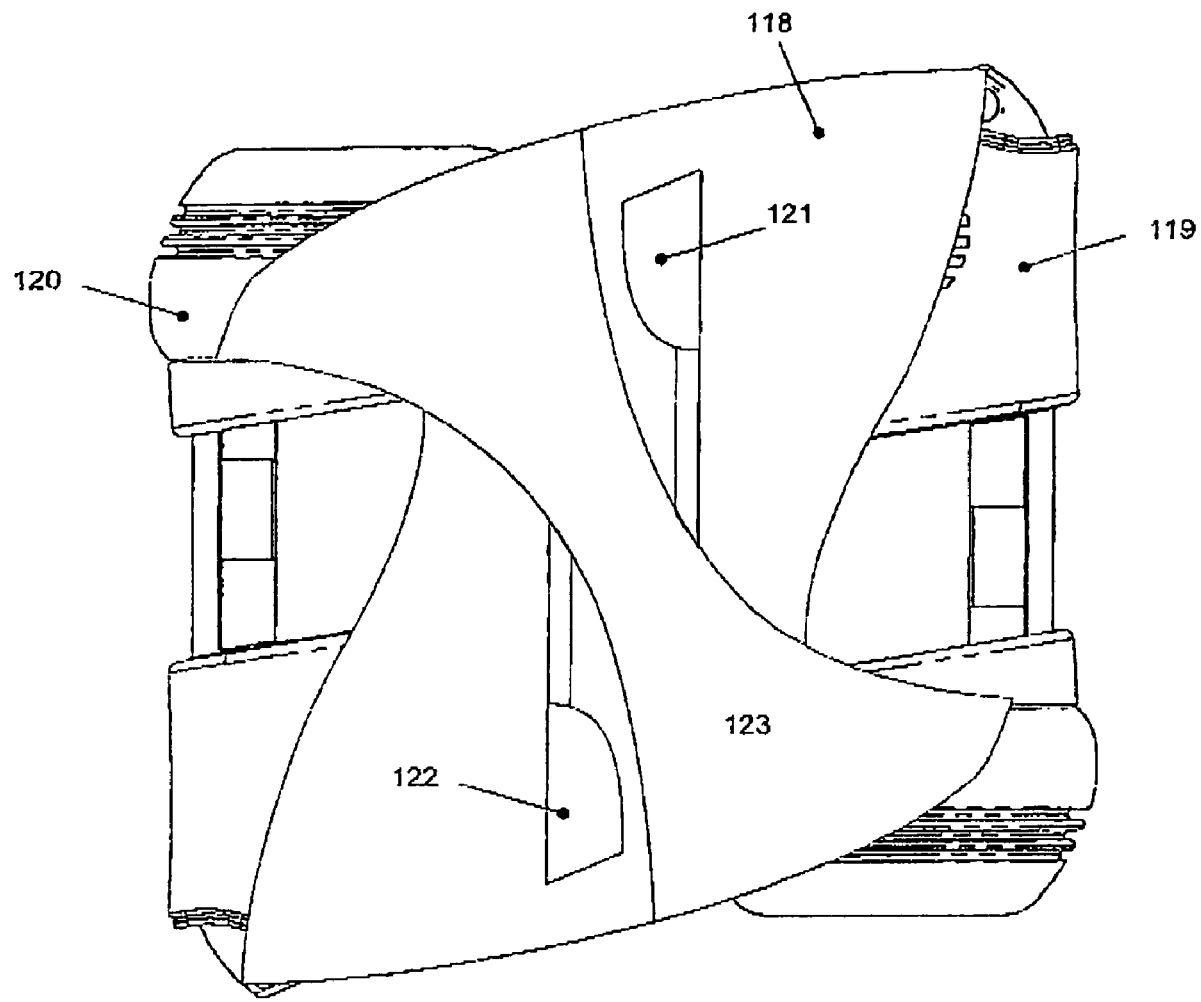
FIG. 25 is front view of an arrangement for holding two medication holders.

FIG. 25 shows a frame 118 designed to receive two medication holders which may also be termed medical housings 119, 120 simultaneously. The housings may be connected to the frame through hooks 121, 122, respectively. The frame 118 may have a loop 123 formed to receive a belt or other carrying arrangement such as a strap.

Figure 26:
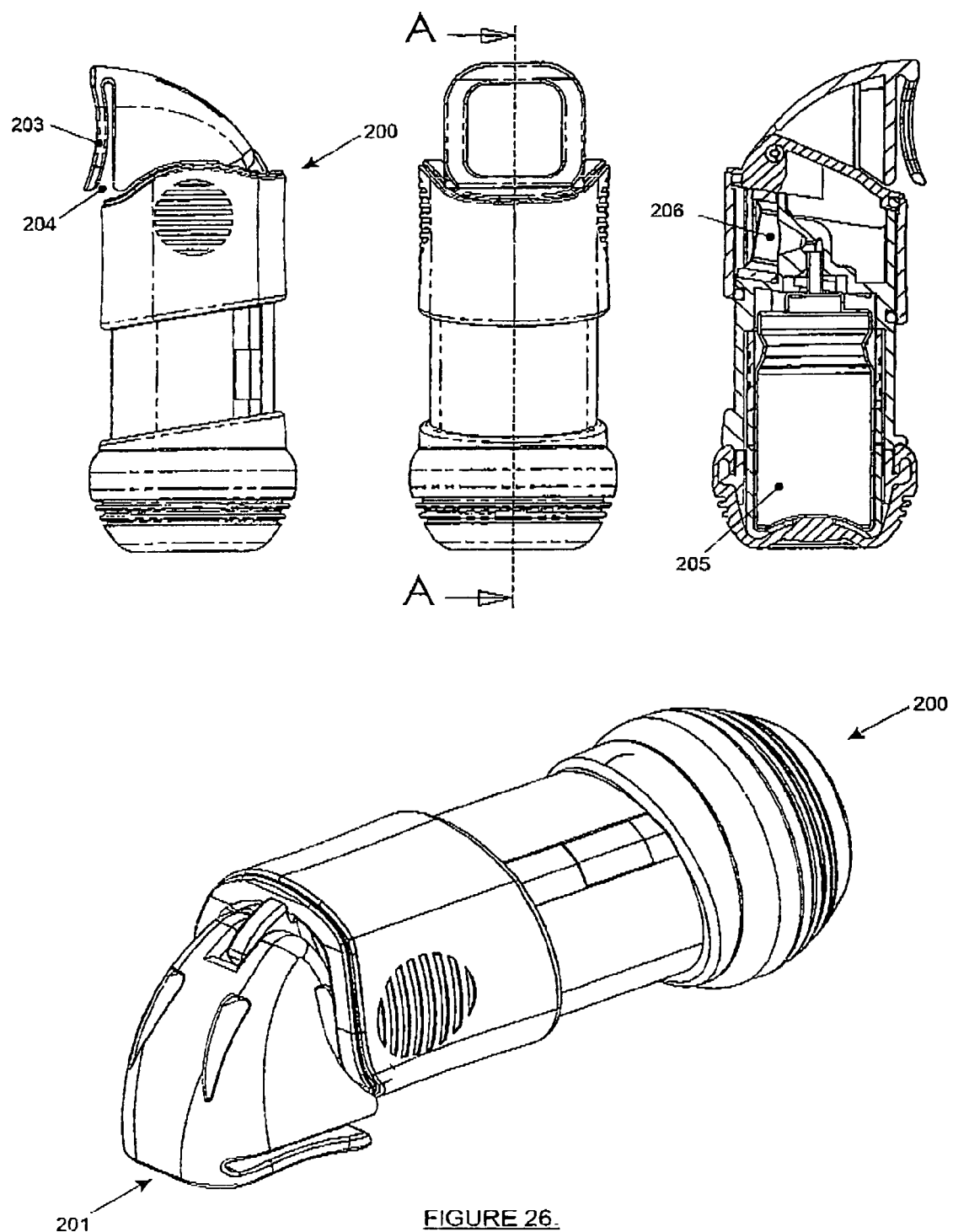
FIG. 26 is a series of views of still another embodiment of a medication holder.

FIG. 26 shows a series of views of a medication holder 200 with a slip on housing support 201 with resilient flap 203 defining slot 204. The housing has an internal canister 205 which discharges into mouthpiece 206.

Figure 27:
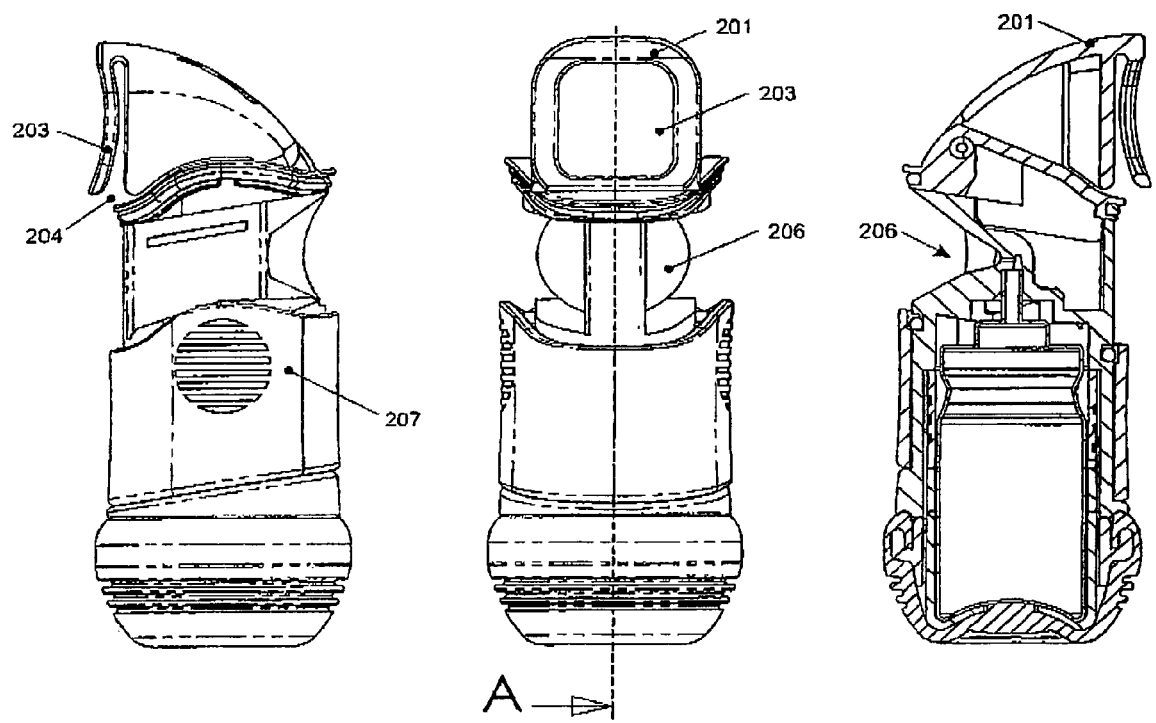
FIG. 27 is a series of views of the medication holder of FIG. 26 when deployed for operation.

The arrangement of FIG. 26 is shown in operation in FIG. 27 where side wall sleeve 207 has been slipped down to reveal the mouthpiece 206 which is positioned below the housing support 201 allowing ready access for a user.

Figure 28:
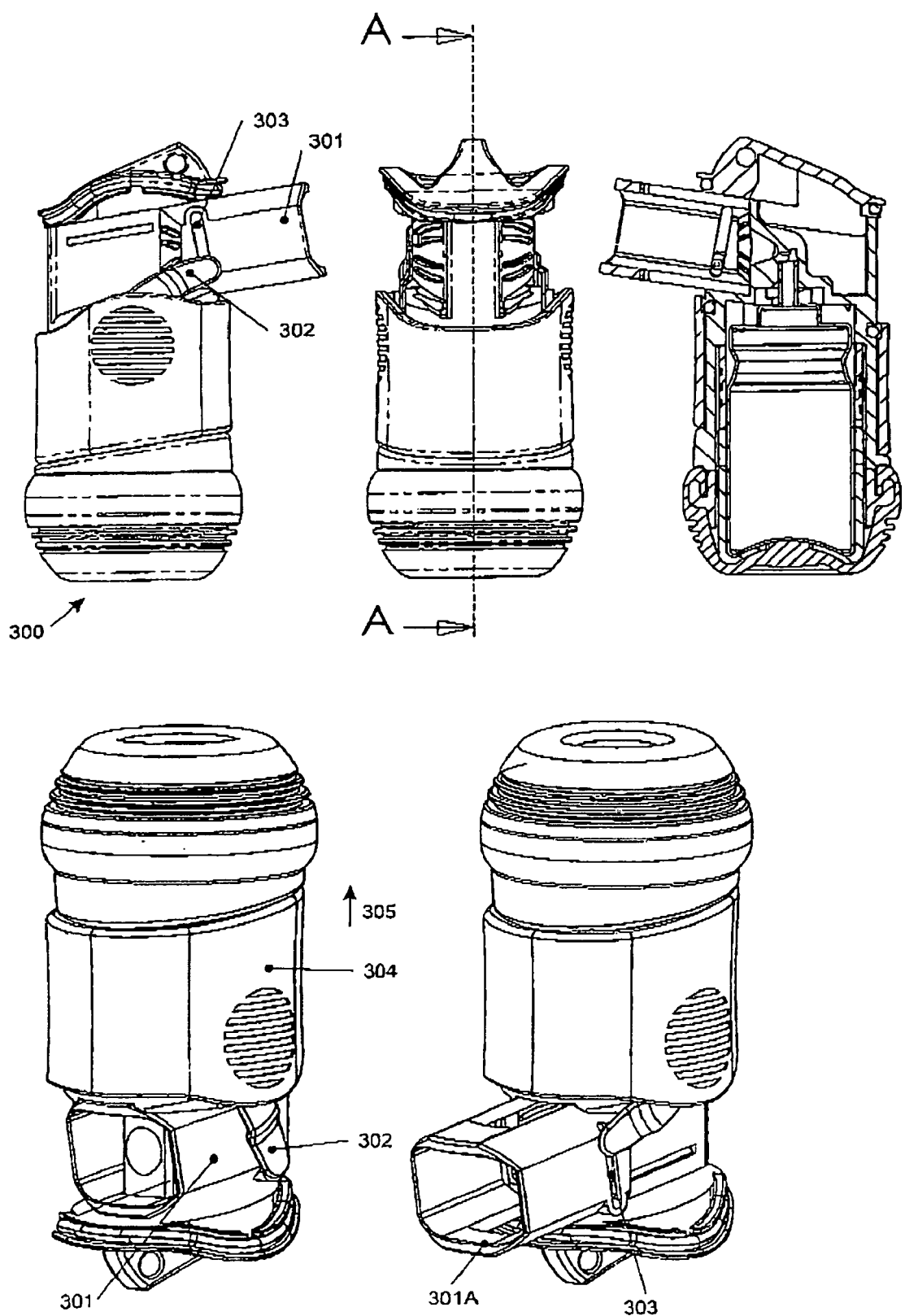
FIG. 28 is a series of views of another embodiment of a medication holder.

FIG. 28 shows a further medication holder 300 with a mouthpiece 301 that is moved in and out of deployment by pivot arm 302 positioned to co-operate with slot 303. In operation, the sleeve 304 is slid in the direction of arrow 305. The mouthpiece 301 is in a retracted stowed position until an internal lug on the sleeve 304 contacts an extension piece of the pivot arm 302 and causes the latter's rotation. As the pivot arm rotates, it leads to deployment of the mouthpiece 301A as it slides up the slot 303. When the sleeve 304 is slid in the reverse direction, it again encounters the extension piece and causes the pivot arm to rotate in the reverse direction, thereby urging the mouthpiece 301 back into its stowed position allowing the sleeve to sit over the top of it and seal it from the environment.

Figure 29:
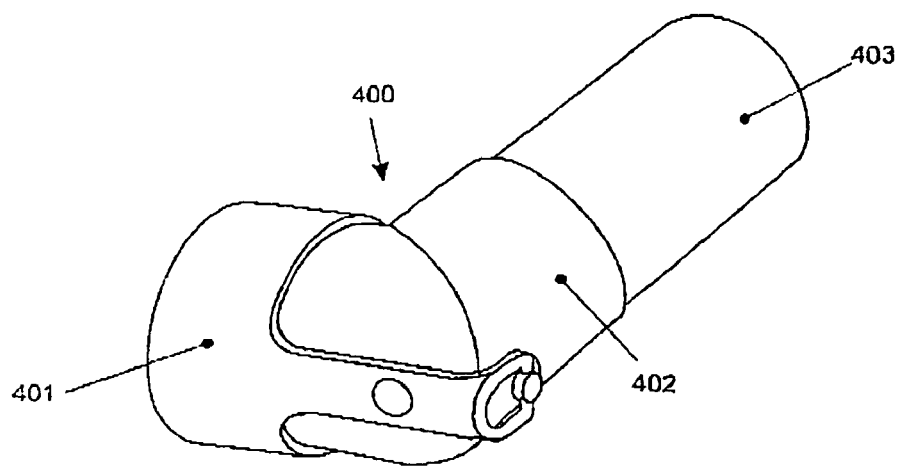
FIG. 29 is a perspective view of a further embodiment of a medication holder.
Figure 30:
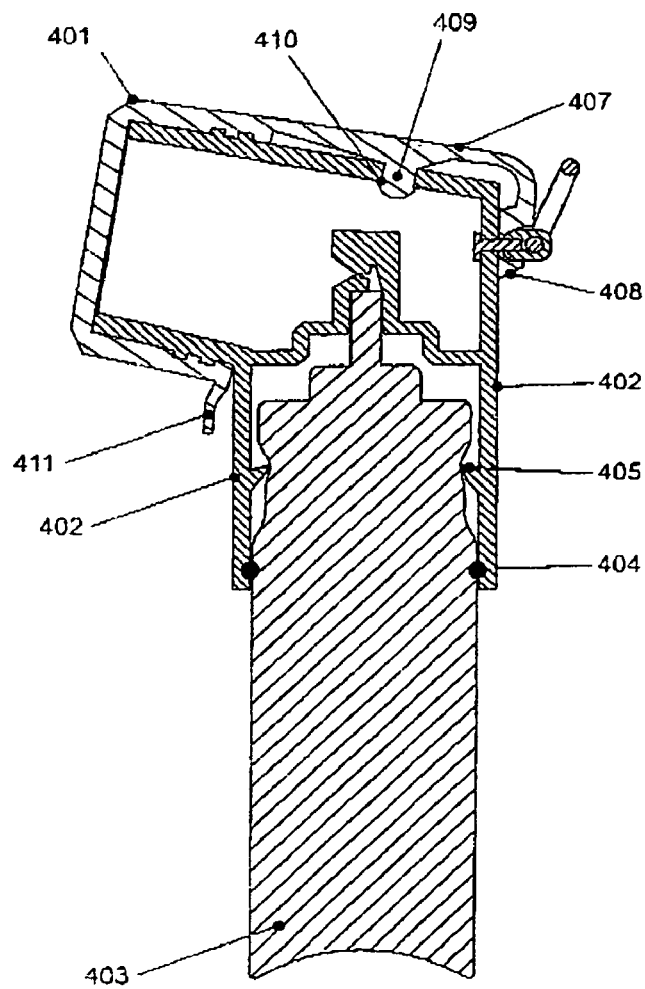
FIG. 30 is a sectional side view of the medication holder of FIG. 29.

FIG. 29 shows a further embodiment of a medication holder having medical housing 400 in which the external wall 401 is formed substantially as a cap to sit over an open bore conduit 402 which receives a medical canister 403. The device is seen in sectional view in FIG. 30, where the open bore of the conduit 402 is closed by the canister 403 and a sealing member 404 in the form of an O ring. An internal ridge 405 may also be provided to assist in retaining the canister 403 in position and to further enhance sealing. The cap 401 is hingedly mounted to the conduit by a strap 407 and binge point 408. The strap 407 has a button 409 designed to locate and occlude aperture 410 in the conduit 402.

In operation, the cap 401 is rotated around and free of the conduit 402 by grasping the tab 411. The cap is removed by pulling the button 409 from the aperture 410 creating an air pathway when used. This overcomes a problem created by the presence of O ring seal 404 which would otherwise prevent passage of air and mixing with an ejected plume of therapeutic agent.

Figure 31:
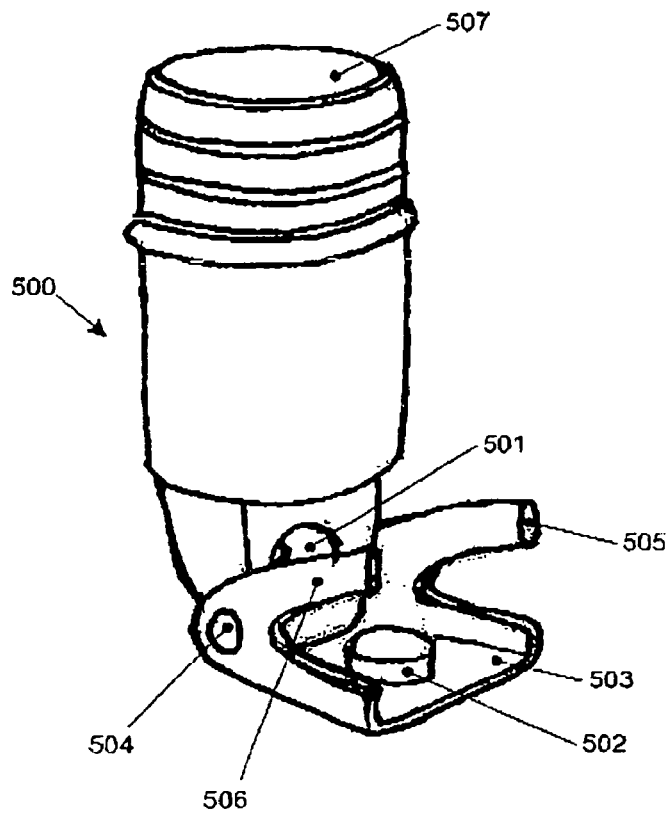
FIG. 31 is a perspective view of a further embodiment of a medication holder of the present invention.
Figure 32:
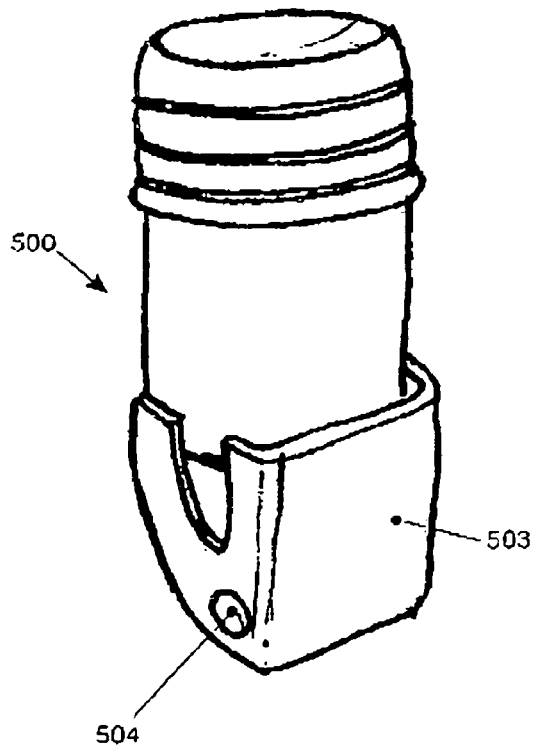
FIG. 32 is a perspective view of the medication holder of FIG. 31 when arranged for storage.

FIGS. 31 and 32 show a further arrangement of a medication holder 500 in which a discharge aperture 501 is closed by button 502 formed on an inside of a flap 503 which is hingedly engaged to the housing through pivot axis 504. In use, the flap 503 may be rotated outwardly as shown in FIG. 31. The flap 503 supports two arms 505, 506 which act to hold a user's lips apart and provide entrance into the oral cavity after discharge from the aperture 501. A user may compress the resilient end 507 to operate an internal canister.

In FIG. 33, a further embodiment of a medication holder with housing 550 is seen in which a slide cap 551 may be removed by pulling it in the direction of arrow 552. The discharge chute or mouthpiece 553 may then move from a rotated position to a deployed position as seen in FIGS. 33A and B. An air, oxygen or gas line 554 provides inspiratory air to mix with the therapeutic agent. Preferably, the oxygen line discharges towards an outlet 555 of the mouthpiece 553. Alternatively or additionally, an auxiliary air inlet aperture 556 may be provided in the mouthpiece 553 and adapted for digital occlusion by a user. Further au inlets 557 may also be provided in the housing 550. A neck cord 559 may be provided to tie the housing around a user's neck or around a limb or anywhere suitable.

The present embodiment is particularly suitable for use with a frangible ampoule. FIG. 33B shows an ampoule 560 in position under a striker 561 designed to rupture the ampoule when brought into contact with it. Sliding of the cap 551 may clear the further air inlets 557 and compress the striker into operative position to rupture the ampoule and release the contents. The contents are preferably a volatile liquid such as methoxyfluorane. The contents may then run down onto evaporative grid 563 which is designed to provide a large evaporation surface area. The grid may be formed by an absorbent open weave cloth fitted into position in the housing 550. Alternatively, the grid may be formed from a number of polymeric vanes locked together to form an effective evaporating arrangement. The grid may form a tortuous airflow pathway to enhance contact between air and volatile agent. The airflow pathway may be serpentine.

A user may commence breathing after rupturing the ampoule and, once used to the sensation of the medication, may occlude the aperture 556 to increase concentration of the agent in the airstream. There are a range of volatile agents which may be suitable for use in the present arrangement. Additional therapeutic gas, oxygen or air may be provided through line 554.

Figure 34:
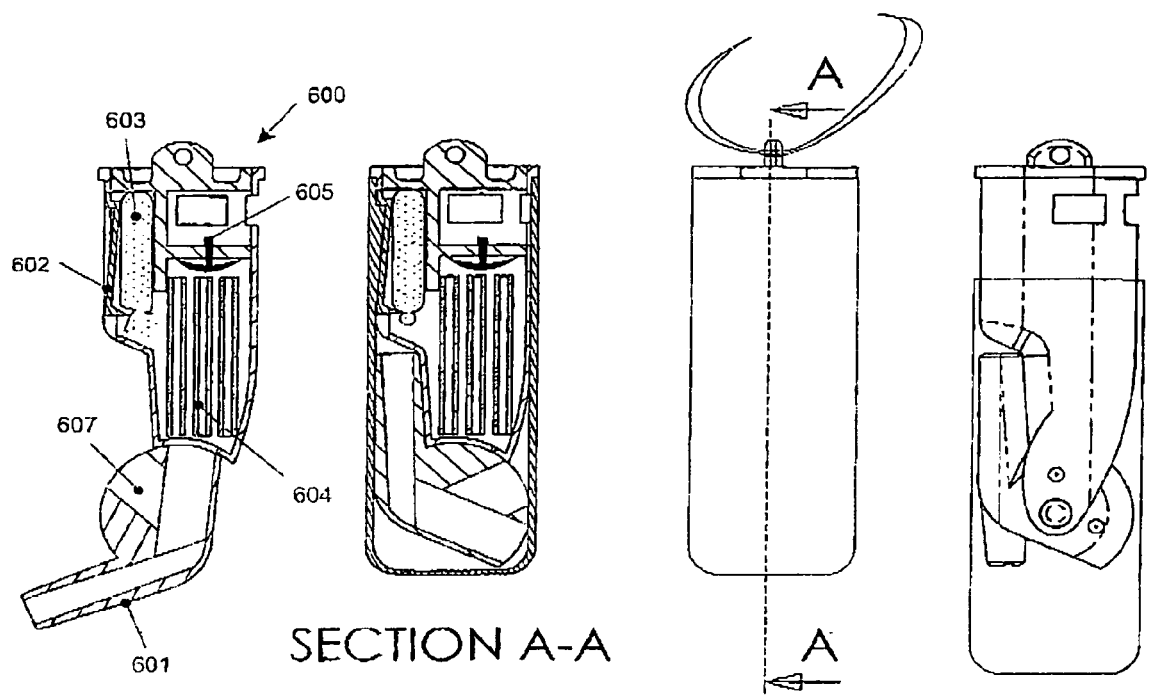
FIG. 34 is a further series of views of the embodiment of FIG. 33.
Figure 34:
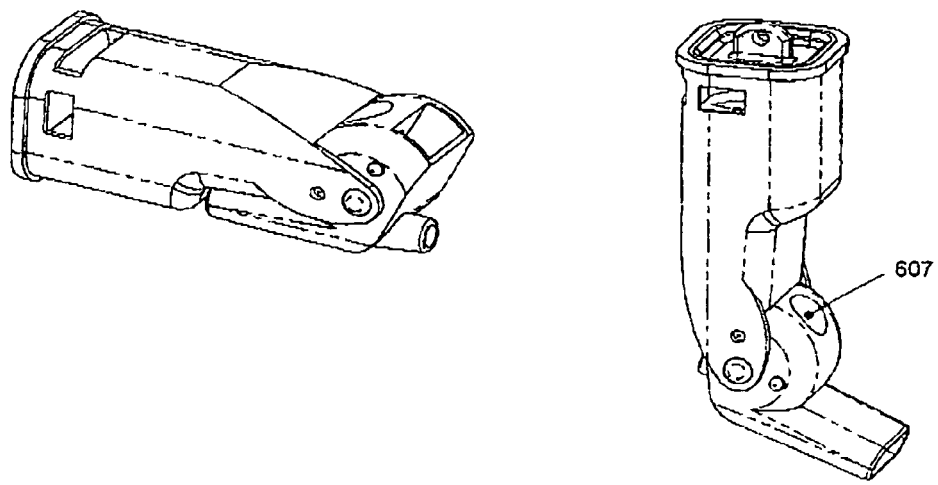
Figure 38:
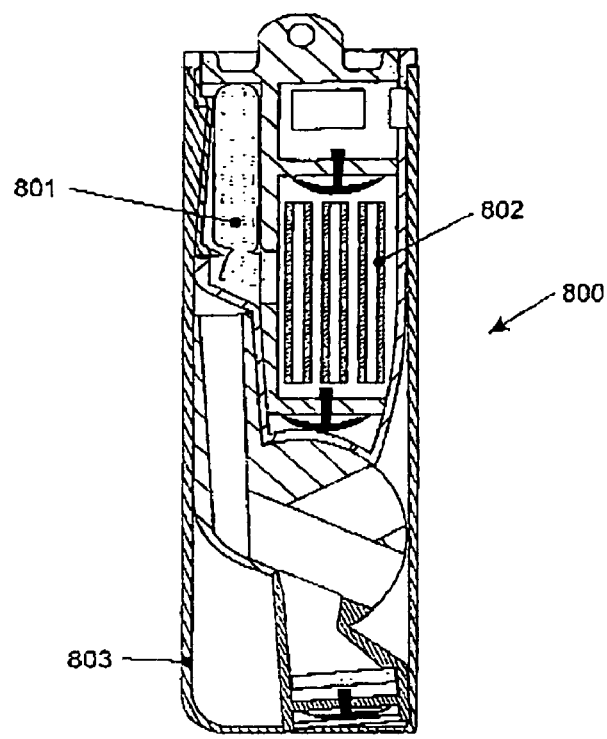
FIG. 38 shows views of an arrangement similar to that of FIG. 34 including a filter acting as an absorber.
Figure 38:
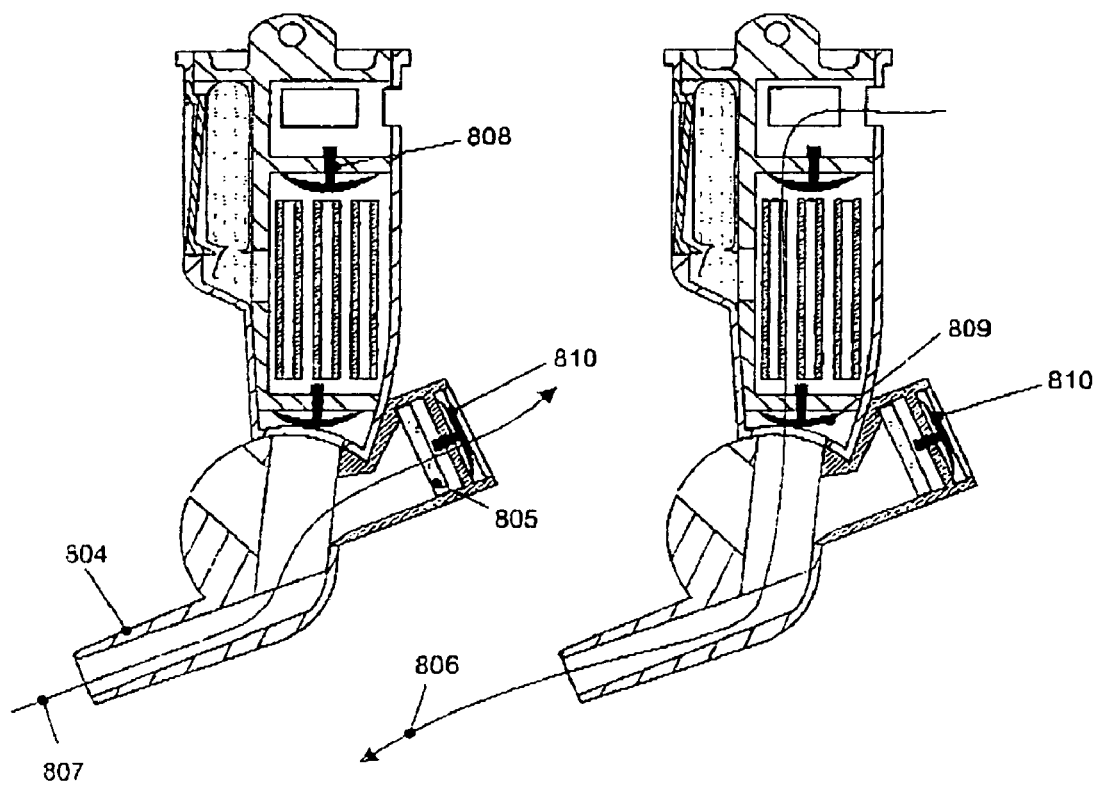

A further view of a similar arrangement is shown in FIG. 34 where the housing 600 has a chute or mouthpiece 601 which rotates into and out of medicating position. A striker 602 is positioned to rupture frangible ampoule 603 and discharge the contents onto the evaporation grid 604. The term "frangible ampoule" may include a vial, container or similar with a frangible section such as a seal. In this embodiment, an inlet one-way valve 605 is provided to prevent loss of the volatile material through the housing. It is also envisaged that the valve may cause air to flow in a preferred direction possibly out of the aperture 607 which may be connected to an enclosed piping channel to direct the discharge air to a scavenger system or to an absorbent system such as charcoal filter. This arrangement prevents or minimizes contamination of the local environment with potentially hazardous or explosive materials in a potentially hazardous situation. This enhances safety for surrounding health workers, particularly when in a confined circumstance such as in an ambulance or hospital cubicle. An example is shown in FIG. 38 where the medication holder has a housing 800 containing an ampoule 801 and evaporation grid 802. Removal of outer cap 803 allows rotation of outlet chute 804 with attached absorber 805. Air is inhaled through pathway 806 and exhaled through expiratory pathway 807 through the absorber 805. Two one-way valves 808, 809 allow air inflow and one one-way valve 810 permits outflow.

Figure 36:
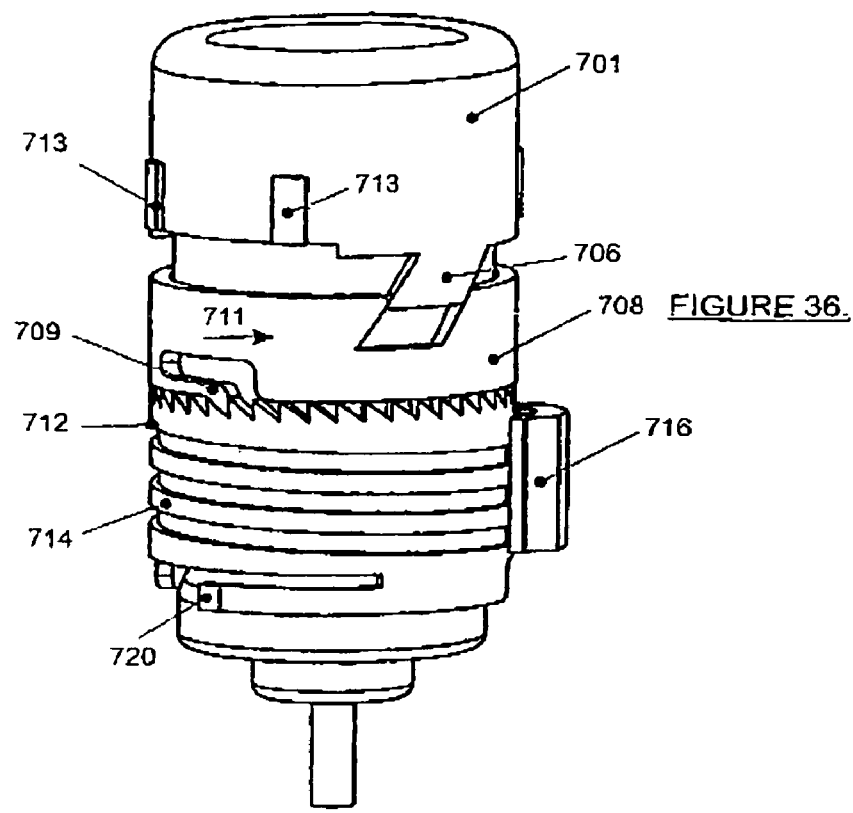
FIG. 36 is a side view of a part of the arrangement of FIG. 35.
Figure 37:
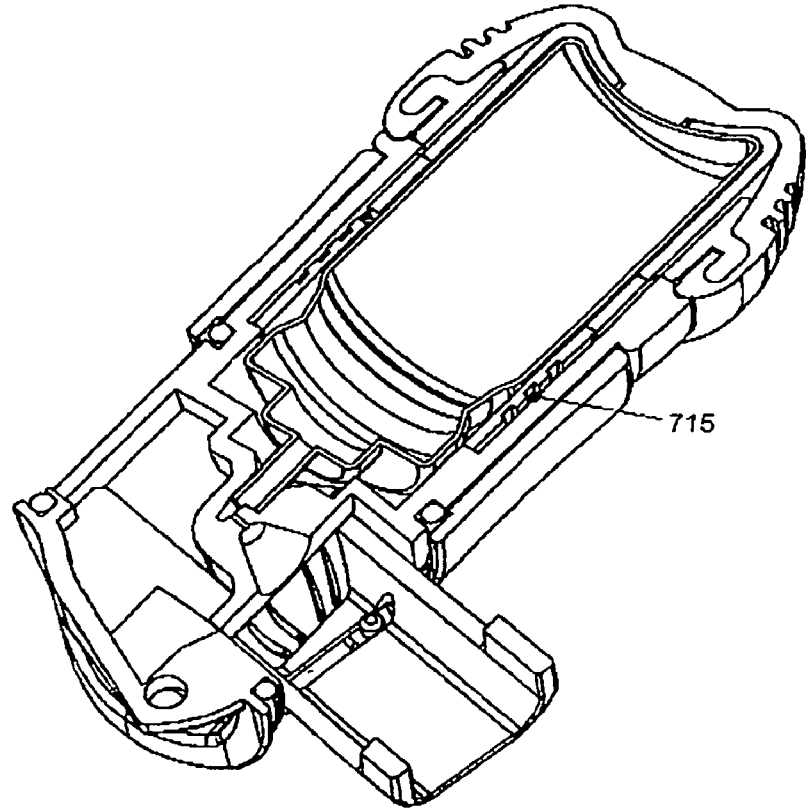
FIG. 37 is a perspective sectional view of a medication holder including the arrangement of FIG. 36.

FIGS. 35, 36 and 37 show a mechanism in a housing 700 for counting or at least indicating the number of times a medical canister has been discharged, even if approximately, thereby providing a user with an indication of the remaining level of therapeutic agent in the device. Referring to FIG. 35B which is an exploded view, there is an end cap 701 and barrel 702. The end cap has a number of resilient claws 703 which interlock with apertured tabs 704 to fix the end cap 701 in position relative to the barrel 702 and prevent relative movement therebetween. The end cap may be removed if required to replace a medication canister or may be locked to prevent reuse. The interlocking arrangement is seen in FIG. 35A. The end cap 701 has one or more tongues 706 adapted to locate in a recess 707 of an internal band 708 positioned inside the barrel. The band 708 supports a flexible finger 709 that terminates in a tooth dimensioned to insert in any one of a number of continuous serrations 710.

Referring to FIG. 36, it can be seen that depression of the end cap 701 causes the tongue 706 which is formed at an angle to urge the band 708 in the direction of arrow 711. This causes the finger 709 to lock into its serration and move the threaded cylinder 712 also in the direction of arrow 711.

Release of the end cap 701 causes it to return to its original position. The presence of tabs 713 prevents rotational movement of the end cap 701 as they mate with corresponding slots in the barrel. As the end cap rises, it pushes the band 708 in the reverse direction to arrow 711 causing the finger to roll over its serration or cammed surface and into the next recess ready for a subsequent use. The external thread 714 co-operates with a corresponding thread 715 which, in turn, co-operates with an indicator mounted in inspection window 716. With rotation of the threaded cylinder 714, the indicator is advanced across a scale which provides an indication of the level of medication in the canister. The scale may be any suitable range of indicia. In a preferred embodiment, the scale is two or more colors ranging preferably from green for full or almost fall through yellow for when the canister is around half full to red indicating the canister should not be used. It is preferred to provide the red coloration when there is still a wide safety margin in the amount of material left in the canister. Any suitable array may be used as an indicator of the canister's suitability for use. The present arrangement may be used for a single canister medication housing which is disposable once the indicator system flags a potential shortage of medication. Alternatively, the present arrangement may be adapted for resetting of the indicator window with subsequent insertion of a new medical canister.

A stop 720 is provided on the cylinder 712. The stop 720 is formed to co-operate with serrations 721 to prevent the cylinder 712 reversing its direction of rotation. That is, the stop allows rotation in a first direction to wind the indicator up but resists operation of the finger 709 from causing the cylinder to rotate backwards.

Figure 39:
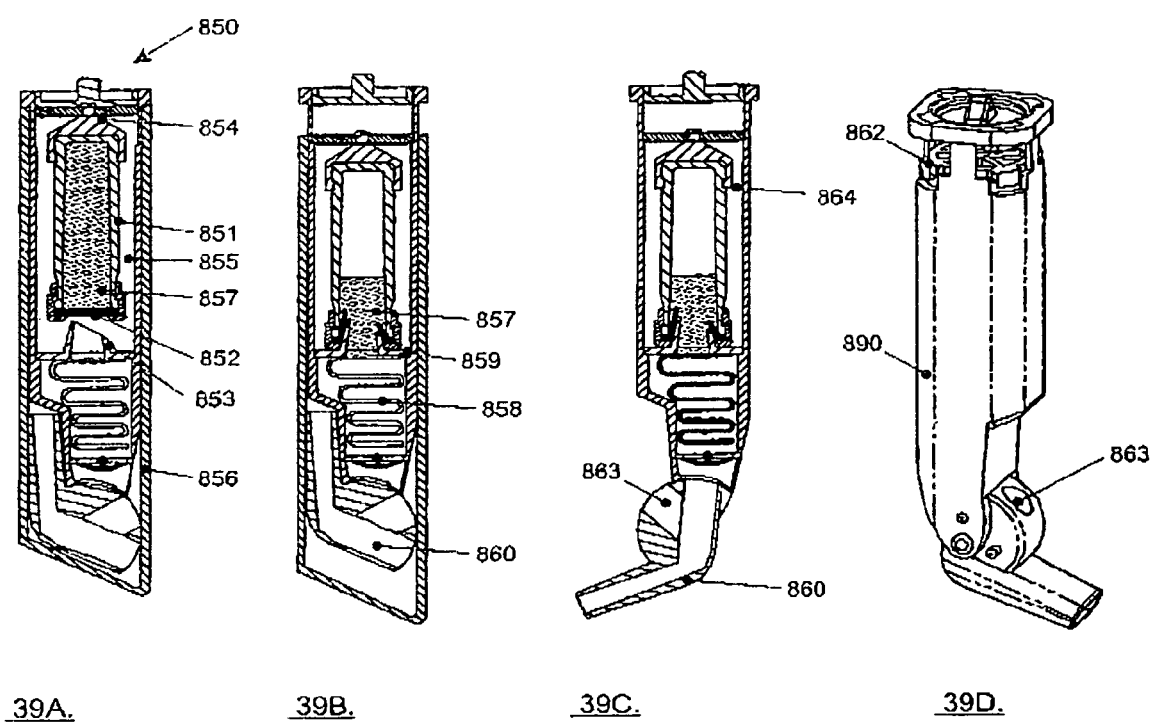
FIGS. 39A-39D is a series of views of a further embodiment of a medication holder.
Figure 40:
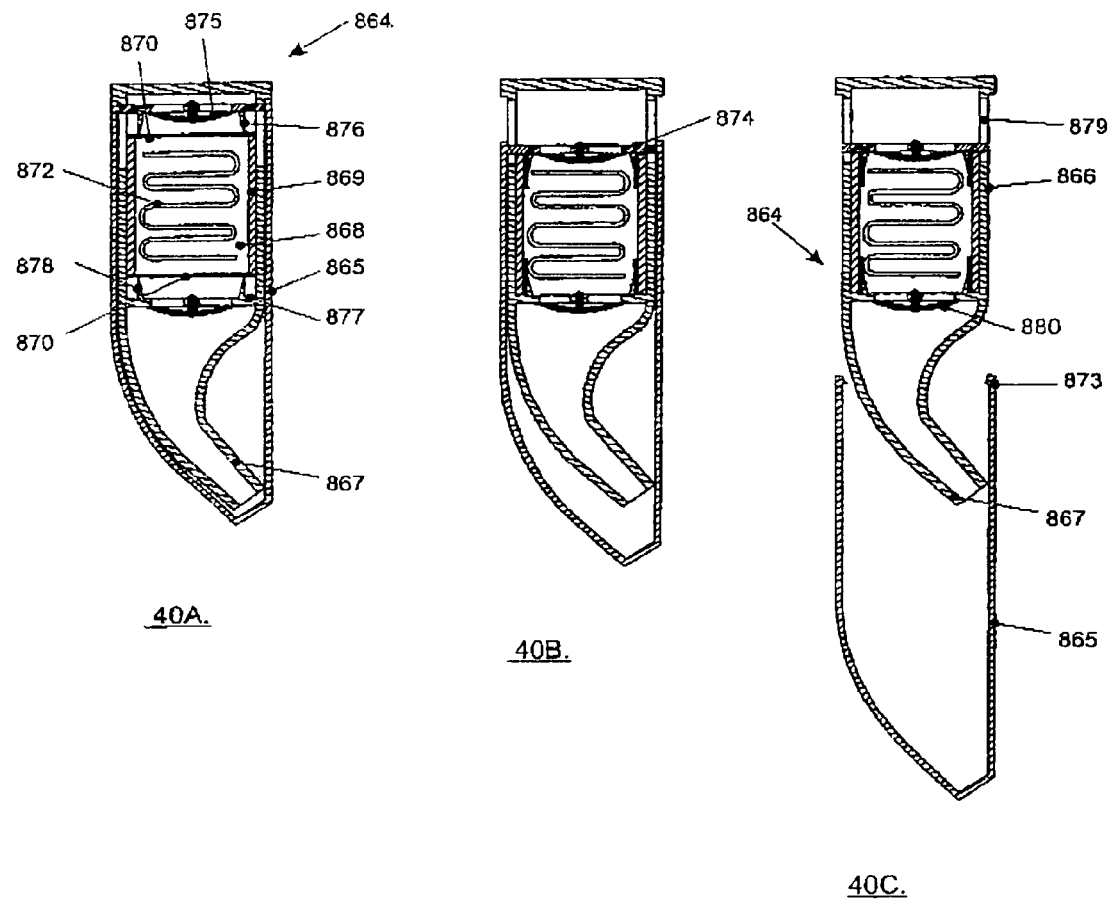
FIGS. 40A-40C is a series of views of yet another embodiment of a medication holder.
Figure 41:
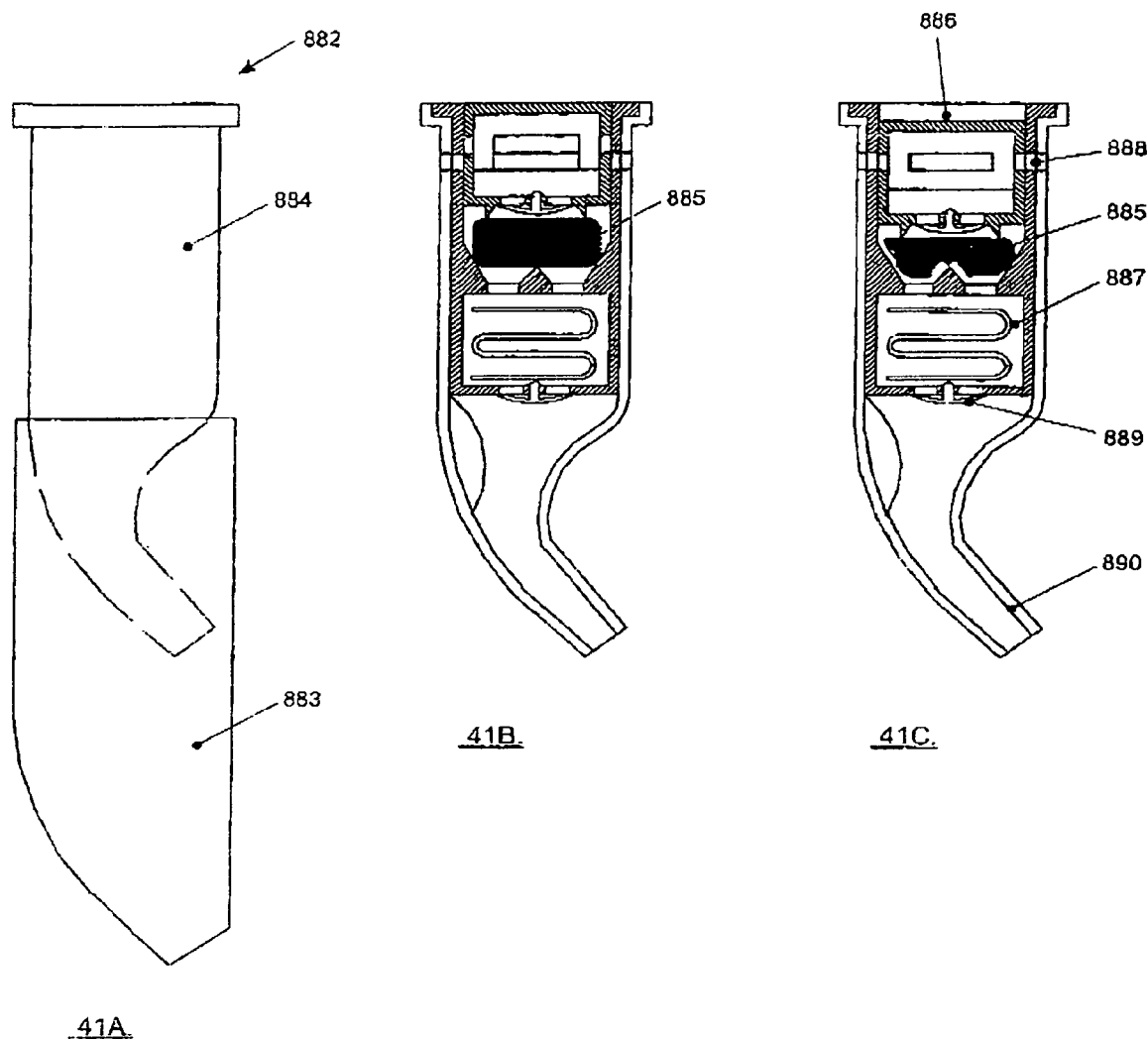
FIGS. 41A-41C is a series of views of still another embodiment of a medication holder.
Figure 42:
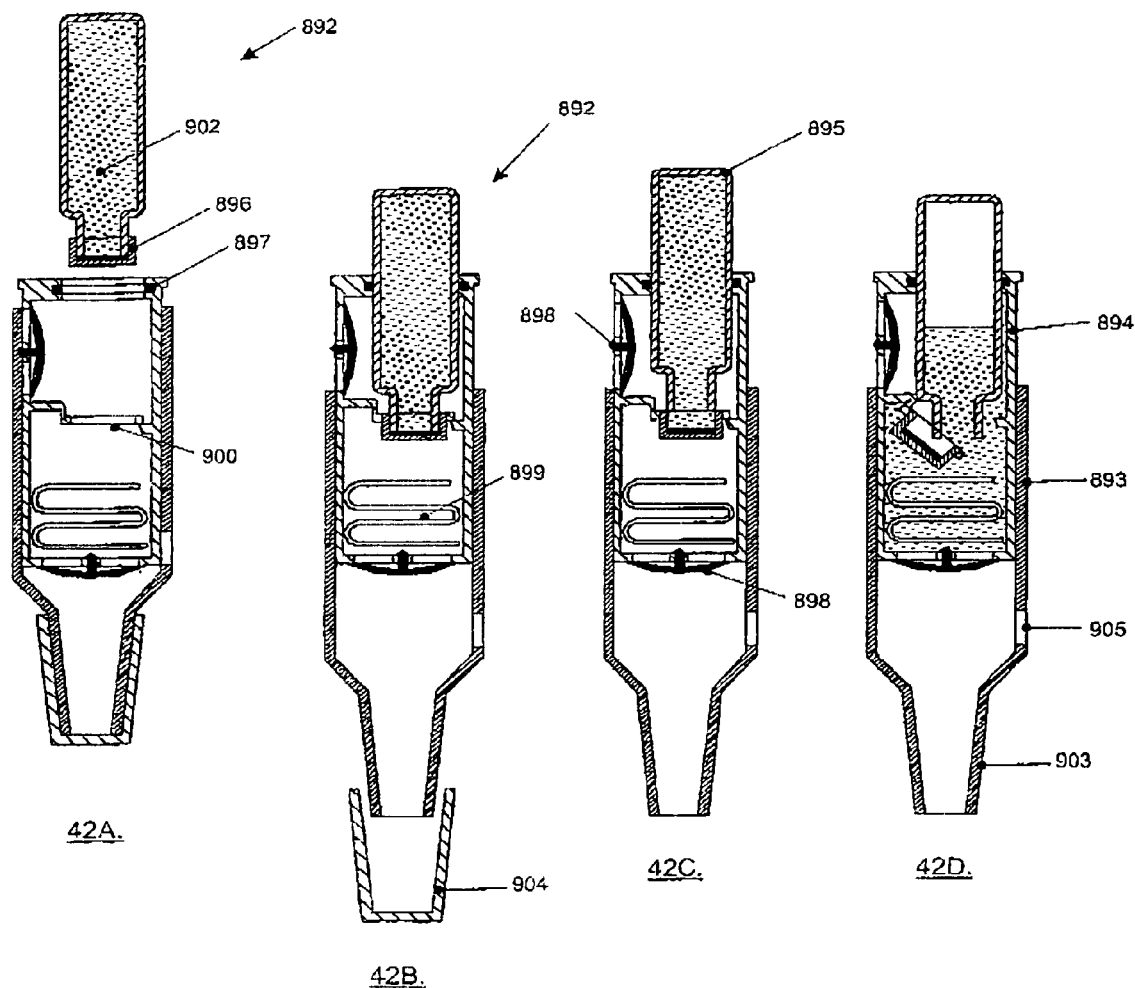
FIGS. 42A-42D is a series of views of yet still another embodiment of a medication holder.
Figure 43:
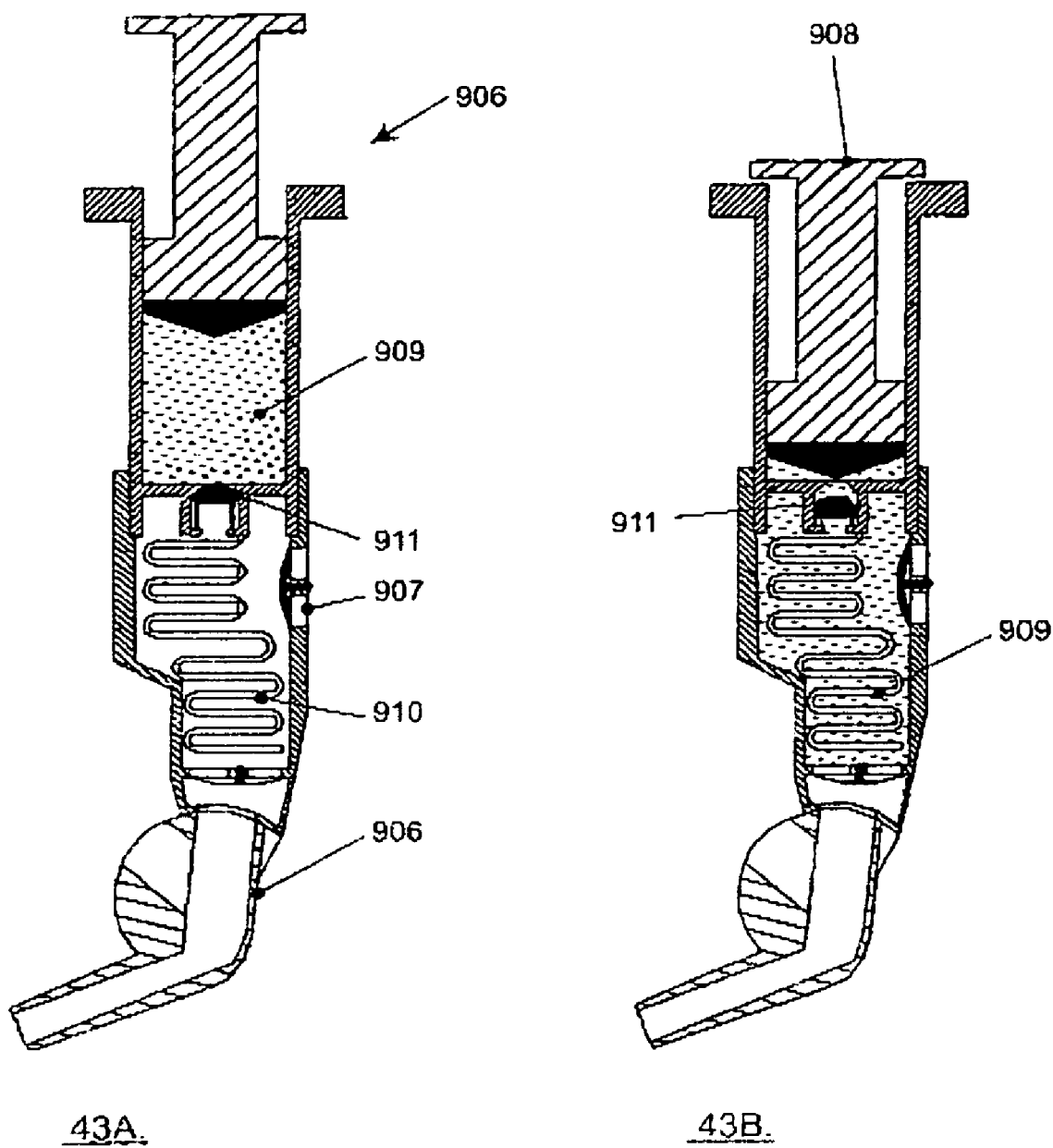
FIGS. 43A-43B is two sectional side views of an alternative medication holder.
Figure 44:
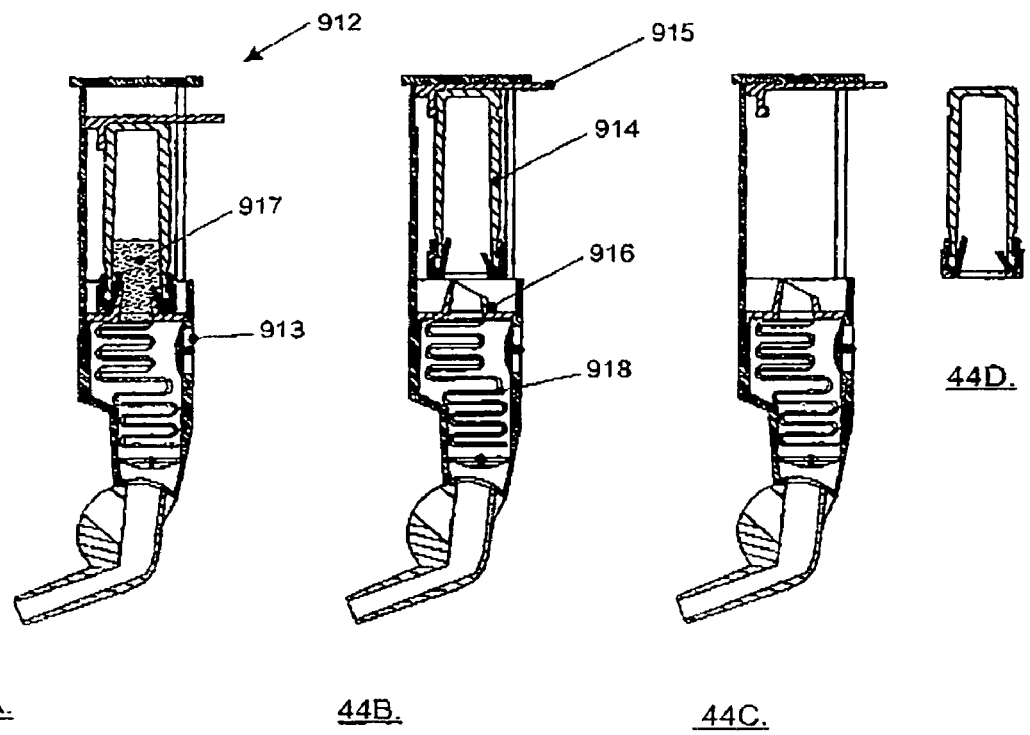
FIGS. 44A-44D is a series of view of a further alternative embodiment of a medication holder.
Figure 45:
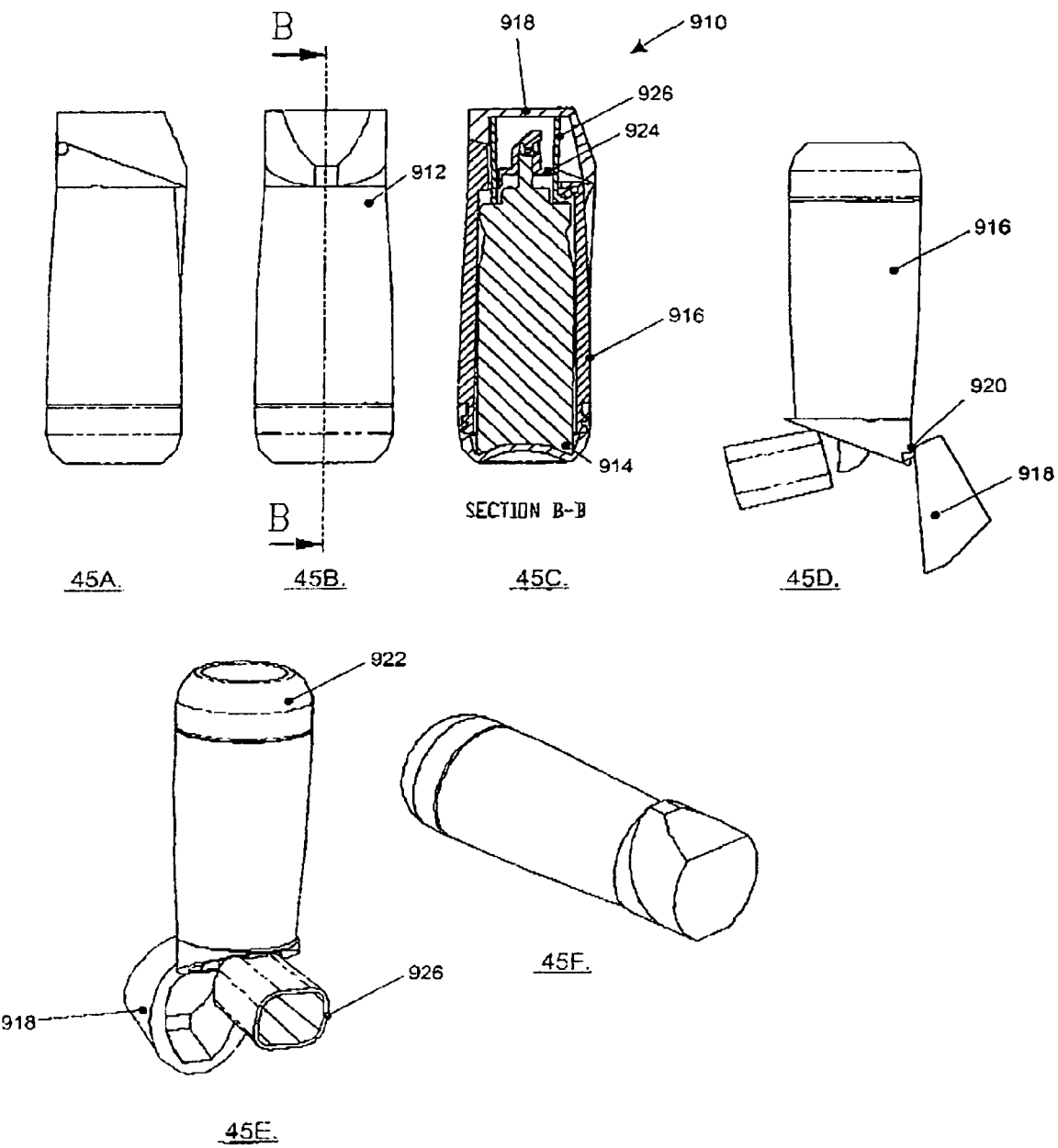
FIGS. 45A-45F shows a medication holder with a flip-top arrangement.
Figure 46:
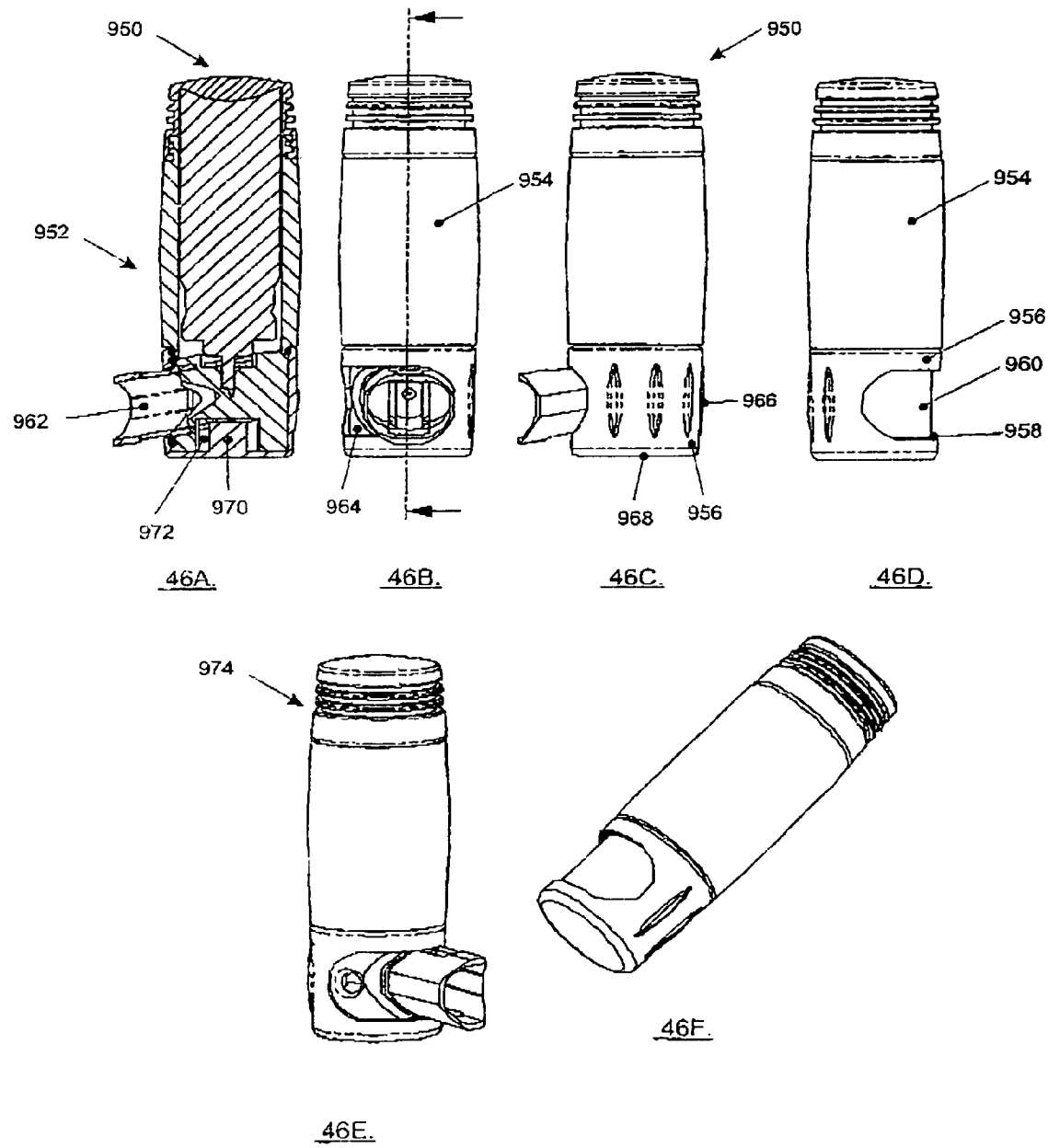
FIGS. 46A-46F shows a series of views of a medication holder with a circumferential sliding or "twist-top" between the inner and outer wall.
Figure 47:
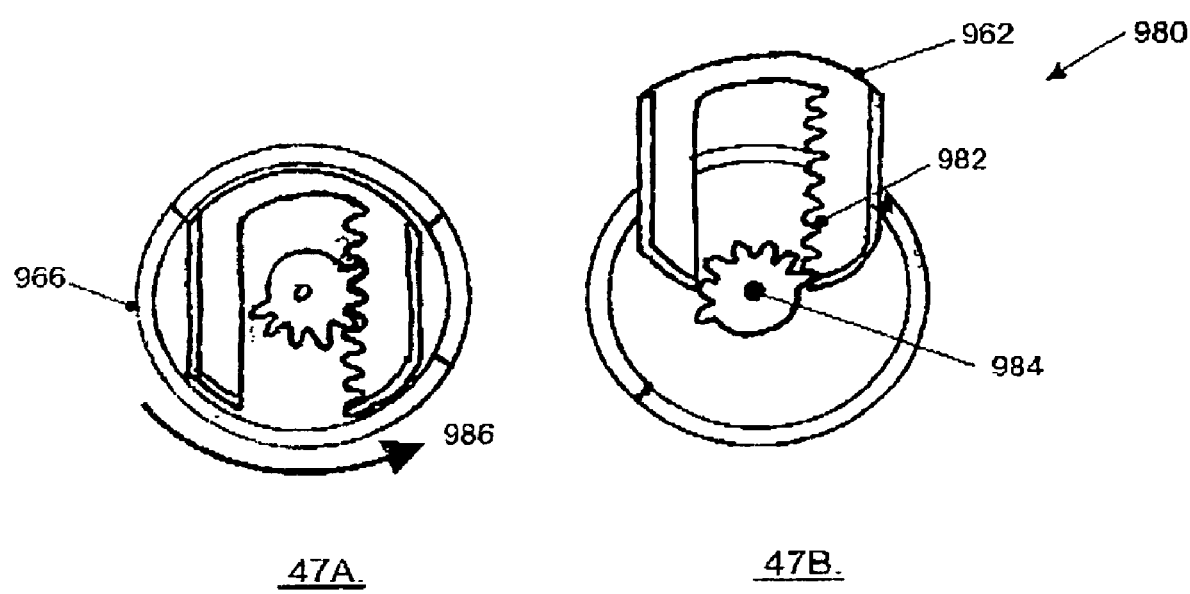
FIGS. 47A-47B shows an arrangement for actuating the mouthpiece of FIG. 46.

In FIG. 39A, a vial 851 is positioned inside a medication holder 850. The vial 851 has a frangible member or section 852 at a lower end and positioned above a punch 853. The vial is held by a cover 854 which is displaceable in the bore 855. The cover 854 is engaged with the outer wall 856 so that downward displacement of the wall will lead to similar motion in the vial. Of course, use of the expression "downward" and like terms is for the purpose of convenience in describing the figures and is not restrictive. The device may be inverted or otherwise positioned during use.

The vial 851 contacts the punch 852 and the membrane is ruptured (FIG. 39B). The membrane may be formed of an elastic material such as rubber or polymeric substance. Alternatively, it may be formed of an alfoil type substance or any other suitable material known to a skilled person.

Once the membrane 852 is ruptured, the liquid medication 857 is dispensed onto an evaporation surface 858 which is shown as a serpentine wall arrangement located in the chamber.

Movement of vial 851 is blocked by internal wall 859. Continued application of a distracting force to the outer wall 856 will disengage the cover 854 from the outer wall, preferably through breaking a weakened connection line. Other mechanisms of connection between the cover and outer wall may be provided, however, it is preferred that they completely seal the device. For example, the cover may have one or more tabs extending into corresponding recesses in the outer wall. The cover may form a snapfit connection with the outer wall.

Application of a distracting force of sufficient strength may fracture or deform the tabs leading to separation of the cover and outer wall.

Once the outer wall 856 is removed from the inner wall 89, the mouthpiece 860 may be rotated into a discharge position as shown in FIG. 39C. Movement of the outer wall 856 also clears air inlets 862, as shown in FIG. 39D.

Application of suction to the mouthpiece 860 results in airflow through the inlet 862, into the chamber or cavity 864, around the vial 851, as cover 854 is air permeable, around the evaporation surface 858, thereby entraining the medication 857 and through the mouthpiece 860 to a recipient.

An auxiliary air inlet 863 allows a user to vary the relative concentration of inhaled medication by use of a digit to partially, totally or intermittently occlude it.

FIG. 40 shows an embodiment of a medication device 864 having an outer wall 865, an inner wall 866 and a fixed mouthpiece 867. In this embodiment, the medication is stored in a medication chamber 868 formed by a continuous side wall 869 and two end seals 870. An evaporation arrangement or surface 872 is positioned inside the chamber 868. The evaporation surface may be formed from a wick type material which may hold the medication by absorption.

A lip 873 is formed in the outer wall and positioned in a recess in an upper wall 874 which supports upper valve 875 and punch 876.

Removal of the outer wall 865 causes the upper wall 874 to slide downwards and compress the chamber 868, urging it onto lower wall 877 and lower punch 878. The punches 876, 878 perforate the seals 870, as shown in FIG. 40B. The lip 873 disengages from the recess in upper wall 874 and allows removal of the outer wall. Removal of the outer wall also clears air inlets 879. The previously sealed medication device now has an air pathway through inlets 879, upper valve 875, medication chamber 868, lower valve 880 and mouthpiece 867. These self-releasing embodiments are particularly suitable for use with volatile agents such as methoxyfluorane in trauma situations.

FIG. 41 shows a medication holder 882 with an outer wall 883 and inner wall 884. Medication is contained in a crushable vial 885. In operation, the outer wall 883 as removed and a plunger 886 depressed to crush the vial and release its contents onto evaporation arrangement 887. Depression of the plunger 886 also causes alignment of air inlets 888 to provide an airflow pathway through the device including valve 889 and fixed mouthpiece 890.

FIG. 42 shows a medication device 892 comprising an outer wall 893 and inner wall 894 which are slidable relative to each other. A vial 895 is provided having a screw cap 896.

The vial 895 may be carried attached to the device 892 or separately. It is mounted through an aperture 897 which may be fitted with a plug when the vial is not in place.

When the outer wall 893 is slid downwards, an air pathway is opened through valve 898 and evaporation arrangement 899. The vial 895 is pushed into a receiving seat 900 which captures the cap 896. The vial is unscrewed from the cap and pushed forwards to dislodge the cap and discharge contents 902 onto arrangement 899 for inhalation through mouthpiece 903. An auxiliary cap 904 and accessory air inlet 905 are also shown.

FIG. 43 shows a medication device 906 in which the outer wall has been removed and is not shown. A rotatable mouthpiece 906 is positioned for use and an air inlet with one-way valve 907 is cleared.

A plunger 908 is depressed to force medication 909 past a spring valve 911 and onto an evaporation arrangement formed by a wick 910. The plunger arrangement may comprise one embodiment of impact means.

FIG. 44 shows a medication device 912 designed for replacement of vials after use. An outer wall has again been removed to clear an air inlet 913. A vial 914 is positioned in a depressible frame 915 which carries the vial onto a punch 916 to release the contents 917 onto evaporation arrangement 918. The vial may be replaced once exhausted.

FIG. 45 shows a medication holder 910 formed by a housing 912 and medication container in the form of canister 914. A first wall 916 abuts a second wall 918 in end-to-end apposition. The second wall 918 forms a flip-top cap as seen in FIG. 45D which is pivotally engaged to the first wall 916 by hinge 920. A flexible end cap 922 is provided to seal an end of the housing 912 and also allow manual compression of the canister 914 against a seat 924 to discharge a dose of medication. Rotation of the cap 918 from a closed position seen in FIG. 45C to an open position seen in FIGS. 45D and 45E also causes a mouthpiece 926 to be rotated from its stowed upright position to a laterally extending position seen in FIG. 45E. In its deployed position, the mouthpiece is accessible to a user and is available for easy access.

FIG. 46 shows a series of views of a filer embodiment of a medication holder 950 comprising a housing 952 formed, in part, by inner wall 954 and outer wall 956. The outer wall 956 forms a collar 966 and end cap 968. The end cap 968 and collar 966 are circumferentially rotatable around the inner wall 954 so that they may be twisted between a closed position shown in FIG. 46D and a position ready for use as seen in FIGS. 46A, 46B, 46C and 46E. The collar 966 has an aperture 958 which, in FIG. 46D, is located over a section 960 of the inner wall 954 in sealing engagement. Rotation of the collar 966 and end cap 968 causes deployment of a mouthpiece 962 by aligning the aperture 958 with an aperture 964 in the inner wall. Rotation also drives a pin 970 in a corresponding groove 972 formed in the mouthpiece to urge the mouthpiece 962 outwardly, preferably along one or more guide rails. Rotation of the collar 966 and end cap 968 in the reverse direction will lead to retraction and storage of the mouthpiece. A flexible end membrane 974 is located on the device to allow manual depression of the canister.

FIG. 47 shows an alternative arrangement 980 for driving the mouthpiece 962 outwardly. It comprises a rack 982 formed in an edge of the mouthpiece and a pinion wheel 984 which is rotated by motion of the collar in the direction of arrow 986 to move from a stowed position as shown in FIG. 47A to a deployed position as shown in FIG. 47B.

Throughout the specification, the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the above appendant claims.

The invention claimed is:

1. A portable medication holder for holding a medication container and discharging a liquid agent therefrom, the portable medication holder comprising:

a housing including a first wall forming at least a part of a chamber;

an air pathway passing through the chamber;

a second wall engaging the first wall, and moveable between a closed position in which the chamber and air pathway are sealed and an open position in which the air pathway is open;

evaporation means to assist in evaporation of the liquid agent into air in the air pathway;

a medication discharge chute for directing the air pathway to a user;

opening means for opening the medication container and releasing the liquid agent to the air in the air pathway; and at least one of one or more one-way valves to provide unidirectional air flow for at least one inspiratory air and expired air.

2. The portable medication holder of claim 1 including the medication container being at least one of located in the chamber or in fluid communication with the chamber.

3. The portable medication holder of claim 2, wherein the medication container is at least one of a vial, ampoule bottle, and canister and is frangible, at least in part.

4. The portable medication holder of claim 3, wherein the liquid agent is methoxyflurane.

5. The portable medication holder of claim 3, wherein the second wall forms at least one of a cover and sleeve.

6. The portable medication holder of claim 3 wherein the opening means is automatically activated by moving the second wall to the open position.

7. The portable medication holder of claim 3, wherein the opening means includes a striker adapted to open the medication container.

8. The portable medication holder of claim 7, wherein the striker is activated by sliding the second wall to the open position.

9. The portable medication holder of claim 3, wherein the opening means includes a punch to open a frangible seal in the container.

10. The portable medication holder of claim 3, wherein the opening means includes a seat to grip a cap, which may be a screw cap, of the container.

11. The portable medication holder of claim 2, wherein the opening means includes a plunger to pressurize and discharge the liquid agent.

12. The portable medication holder of claim 2, wherein the evaporation means comprises a wick material.

13. The portable medication holder of claim 2, wherein the evaporation means comprises at least one of an evaporation plate, evaporation plates, and a grid.

14. The portable medication holder of claim 2, wherein the evaporation means forms a serpentine or tortuous path as part of the air pathway.

15. The portable medication holder of claim 1, wherein the medication chute is rotatable between a stowed position and a deployed position.

16. The portable medication holder of claim 1, wherein the medication chute further includes a gas line for delivering a respiratory gas.

17. The portable medication holder of claim 1, wherein the medication chute includes an auxiliary air inlet adapted for occlusion by a digit of a user.

18. The portable medication holder of claim 1, further including one or more wherein at least one of one or more one-way valves are in the intake air pathway to provide unidirectional inspiratory airflow of inspiratory air.

19. The portable medication holder of claim 18, wherein the medication chute is in fluid connection with an outlet one-way valve for expired air and the one or more one-way valves include an outlet one-way valve for expired air and are in fluid communication with the medication chute.

20. The portable medication holder of claim 19, wherein the medication chute is in fluid connection with a filter for removing medication from expired air.

21. The portable medication holder of claim 2, wherein the portable medication holder is sealed against the external environment when not in use.

22. The portable medication holder of claim 6 including a strap, preferably a wrist strap, attached to the second wall.

23. The portable medication holder of claim 2, wherein the opening means opens the medication container and releases the liquid agent to the evaporation means.

24. The portable medication holder of claim 2, wherein the evaporation means is an evaporation surface inside the medication container.

25. The portable medication holder of claim 16, wherein the evaporation surface is formed by at least one of an absorbent material and wick.

* * * * *